(12) United States Patent
Boyden et al.

(10) Patent No.: US 9,095,436 B2
(45) Date of Patent: Aug. 4, 2015

(54) ADJUSTABLE ORTHOPEDIC IMPLANT AND METHOD FOR TREATING AN ORTHOPEDIC CONDITION IN A SUBJECT

(75) Inventors: Edward S. Boyden, Cambridge, MA (US); Gregory J. Della Rocca, Columbia, MO (US); Roderick A. Hyde, Redmond, WA (US); Jordin T. Kare, Seattle, WA (US); Eric C. Leuthardt, St. Louis, MO (US); Paul Santiago, St. Louis, MO (US); Todd J. Stewart, St. Louis, MO (US)

(73) Assignee: The Invention Science Fund I, LLC, Bellevue, WA (US)

( * ) Notice: Subject to any disclaimer, the term of this patent is extended or adjusted under 35 U.S.C. 154(b) by 787 days.

(21) Appl. No.: 12/386,269

(22) Filed: Apr. 14, 2009

(65) Prior Publication Data
US 2010/0262239 A1   Oct. 14, 2010

(51) Int. Cl.
| A61B 17/68 | (2006.01) |
| A61F 2/30 | (2006.01) |
| A61F 2/32 | (2006.01) |
| A61F 2/38 | (2006.01) |
(Continued)

(52) U.S. Cl.
CPC . *A61F 2/30* (2013.01); *A61B 17/68* (2013.01); *A61F 2/32* (2013.01); *A61F 2/38* (2013.01); *A61F 2/40* (2013.01); *A61F 2/42* (2013.01); *A61F 2/44* (2013.01); *A61F 2002/3067* (2013.01); *A61F 2002/30537* (2013.01); *A61F 2002/4666* (2013.01); *A61F 2002/48* (2013.01); *A61F 2250/0002* (2013.01); *A61F 2250/0004* (2013.01)

(58) Field of Classification Search
CPC ...... A61B 17/025; A61B 17/60; A61B 17/66; A61B 17/663; A61B 2017/0256; A61B 2017/0268; A61B 2017/0257; A61F 2002/74; A61F 2002/701
USPC ......... 606/251–260, 299, 320, 282, 279, 900, 606/61; 623/2.73, 2.39, 13.11–22.19, 623/23.45, 23.47, 38, 45, 11.11
See application file for complete search history.

(56) References Cited

U.S. PATENT DOCUMENTS

| 4,543,955 A | 10/1985 | Schroeppel |
| 4,850,372 A | 7/1989 | Ko et al. |
(Continued)

FOREIGN PATENT DOCUMENTS

| JP | 2002-248081 A | 9/2002 |
| JP | 2005-501588 A | 1/2005 |
(Continued)

OTHER PUBLICATIONS

IEEE transactions on ultrasonics, ferroelectrics and Frequency control Jack Judy, Dennis Polla, William Robbins vol. 37 No. 5 Sep. 1990.*

(Continued)

*Primary Examiner* — David Bates
*Assistant Examiner* — Samuel Hanna

(57) ABSTRACT

An orthopedic implant is described including at least one adjustment mechanism configured for securing to at least one orthopedic structure of a subject, and at least one motor operatively connected to the at least one adjustment mechanism, wherein the at least one motor is configured to move the at least one adjustment mechanism in at least three degrees of freedom.

33 Claims, 6 Drawing Sheets

(51) Int. Cl.
  *A61F 2/40* (2006.01)
  *A61F 2/42* (2006.01)
  *A61F 2/44* (2006.01)
  *A61F 2/46* (2006.01)
  *A61F 2/48* (2006.01)

(56) References Cited

U.S. PATENT DOCUMENTS

| | | | |
|---|---|---|---|
| 5,041,092 A | 8/1991 | Barwick | |
| 5,156,605 A | 10/1992 | Pursley et al. | |
| 5,415,660 A | 5/1995 | Campbell et al. | |
| 5,575,790 A | 11/1996 | Chen et al. | |
| 5,971,984 A | 10/1999 | Taylor et al. | |
| 6,032,677 A | 3/2000 | Blechman et al. | |
| 6,033,412 A | 3/2000 | Losken et al. | |
| 6,063,121 A * | 5/2000 | Xavier et al. | 623/17.15 |
| 6,164,284 A | 12/2000 | Schulman et al. | |
| 6,383,185 B1 | 5/2002 | Baumgart | |
| 6,450,946 B1 | 9/2002 | Forsell | |
| 6,486,588 B2 | 11/2002 | Doron et al. | |
| 6,694,180 B1 | 2/2004 | Boesen | |
| 6,706,042 B2 | 3/2004 | Taylor | |
| 6,730,087 B1 | 5/2004 | Butsch | |
| 6,835,207 B2 | 12/2004 | Zacouto et al. | |
| 6,880,085 B1 | 4/2005 | Balczewski et al. | |
| 6,940,209 B2 | 9/2005 | Henderson | |
| 7,011,624 B2 | 3/2006 | Forsell | |
| 7,016,735 B2 | 3/2006 | Imran et al. | |
| 7,052,488 B2 | 5/2006 | Uhland | |
| 7,083,650 B2 * | 8/2006 | Moskowitz et al. | 623/17.11 |
| 7,170,214 B2 | 1/2007 | Henderson et al. | |
| 7,309,943 B2 | 12/2007 | Henderson et al. | |
| 7,339,306 B2 | 3/2008 | Henderson | |
| 7,344,541 B2 | 3/2008 | Haines et al. | |
| 7,559,951 B2 | 7/2009 | DiSilvestro et al. | |
| 2002/0198604 A1 * | 12/2002 | Schulman et al. | 623/25 |
| 2003/0124480 A1 | 7/2003 | Peacock, III | |
| 2003/0130616 A1 | 7/2003 | Steil et al. | |
| 2003/0157474 A1 | 8/2003 | Hansen et al. | |
| 2004/0122305 A1 | 6/2004 | Grimm et al. | |
| 2004/0152970 A1 | 8/2004 | Hunter et al. | |
| 2004/0167625 A1 * | 8/2004 | Beyar et al. | 623/11.11 |
| 2004/0209218 A1 | 10/2004 | Chishti et al. | |
| 2005/0052098 A1 | 3/2005 | Henderson | |
| 2005/0203517 A1 | 9/2005 | Jahng et al. | |
| 2005/0208095 A1 | 9/2005 | Hunter et al. | |
| 2005/0234448 A1 | 10/2005 | McCarthy | |
| 2005/0234555 A1 * | 10/2005 | Sutton et al. | 623/17.15 |
| 2005/0258714 A1 | 11/2005 | Henderson et al. | |
| 2005/0261769 A1 * | 11/2005 | Moskowitz et al. | 623/17.11 |
| 2005/0267353 A1 | 12/2005 | Marquart et al. | |
| 2006/0036259 A1 | 2/2006 | Carl et al. | |
| 2006/0036323 A1 | 2/2006 | Carl et al. | |
| 2006/0049720 A1 * | 3/2006 | Henderson et al. | 310/328 |
| 2006/0069447 A1 * | 3/2006 | DiSilvestro et al. | 623/23.16 |
| 2006/0079898 A1 | 4/2006 | Ainsworth et al. | |
| 2006/0136062 A1 | 6/2006 | DiNello et al. | |
| 2006/0173238 A1 | 8/2006 | Starkebaum | |
| 2006/0247722 A1 | 11/2006 | Maschino et al. | |
| 2006/0252983 A1 | 11/2006 | Lembo et al. | |
| 2006/0271112 A1 * | 11/2006 | Martinson et al. | 607/2 |
| 2007/0010868 A1 | 1/2007 | Ferren et al. | |
| 2007/0021458 A1 | 1/2007 | Ishikawa et al. | |
| 2007/0156013 A1 | 7/2007 | Birk | |
| 2007/0161872 A1 | 7/2007 | Kelly et al. | |
| 2007/0161888 A1 | 7/2007 | Sherman et al. | |
| 2007/0168036 A1 | 7/2007 | Ainsworth et al. | |
| 2007/0169567 A1 | 7/2007 | Schulz et al. | |
| 2007/0179493 A1 | 8/2007 | Kim | |
| 2007/0179615 A1 * | 8/2007 | Heinz et al. | 623/17.12 |
| 2007/0219561 A1 | 9/2007 | Lavallee et al. | |
| 2007/0250172 A1 * | 10/2007 | Moskowitz et al. | 623/17.15 |
| 2007/0255286 A1 * | 11/2007 | Trieu | 606/90 |
| 2007/0276378 A1 | 11/2007 | Harrison et al. | |
| 2008/0065225 A1 * | 3/2008 | Wasielewski et al. | 623/18.11 |
| 2008/0183134 A1 | 7/2008 | Vignery et al. | |
| 2008/0195156 A1 | 8/2008 | Ainsworth et al. | |
| 2008/0254416 A1 | 10/2008 | Claudinon et al. | |
| 2008/0294269 A1 | 11/2008 | Fell | |
| 2009/0076597 A1 | 3/2009 | Dahlgren et al. | |
| 2009/0187120 A1 * | 7/2009 | Nycz | 600/587 |
| 2009/0234456 A1 * | 9/2009 | Nycz | 623/17.16 |
| 2010/0070033 A1 * | 3/2010 | Doty | 623/17.16 |
| 2010/0318116 A1 * | 12/2010 | Forsell | 606/200 |

FOREIGN PATENT DOCUMENTS

| | | |
|---|---|---|
| JP | 2006-218234 A | 8/2006 |
| JP | 2008-504590 A | 2/2008 |
| WO | WO 2005/119610 A1 | 12/2005 |

OTHER PUBLICATIONS

Linear piezoelectric stepper motor.*
ADXL330-0 data sheet.*
NPL for Jack Judy, Dennis Polla & William Robbins.*
UK Intellectual Property Office Combined Search and Examination Report Under Section 17 & 18(3); App. No. GB1109072.7; bearing a date of Sep. 22, 2011 (received by our agent on Sep. 26); pp. 1-3.
UK Intellectual Property Office Examination Report Under Section 18(3); App. No. GB0916445.0; Jan. 4, 2011 (received by our Agent on Jan. 5, 2011); pp. 1-2.
"Hydrocephalus, NPH Treatment"; Medtronic.com; bearing a date of 2007; printed on Feb. 20, 2007; pp. 1-2; Medtronic Inc.; located at http://www.medtronic.com/hydrocephalus/nph/nph_subs/nph_treatment.html.
Qian, Haifeng; Loizou, Philipos C.; Dorman, Michael F.; "A Phone-Assistive Device Based on Bluetooth Technology for Cochlear Implant Users"; IEEE Transactions on Neural Systems and Rehabilitation Engineering; bearing a date of 2003; pp. 282-287; IEEE.
PCT International Search Report; International App. No. PCT/US 10/01119; bearing a date of Jun. 17, 2010; pp. 1-2.
Squiggle Motors; New Scale Technologies, Inc.; pp. 1-4; www.newscaletech.com.
Squiggle motors—miniature piezo motors; New Scale Technologies, Inc.; pp. 1-4; downloaded on Oct. 17, 2008 from http://www.newscaletech.com/squiggle_overview.html.
Useful Articles and Papers; New Scale Technologies, Inc.; p. 1; downloaded on Oct. 23, 2008 from hup://www.newscaletech.com/article_papers.html#HearingAidPaper.
Japanese Office Action; App. No. 2009-550890 (Based on PCT/US2008/002011); received by our agent on Aug. 21, 2012; pp. 1-2.

* cited by examiner

ADJUSTABLE ORTHOPEDIC IMPLANT AND METHOD FOR TREATING AN ORTHOPEDIC CONDITION IN A SUBJECT

SUMMARY

An orthopedic implant described herein allows a surgeon to control certain movements of at least a portion of the implant in multiple degrees of freedom during surgery or post-operatively. Post-operatively, the surgeon may transcutaneously control the orthopedic implant to vary a configuration of an internal orthopedic structure in the subject. The surgeon may utilize the orthopedic implant to control growth and healing of the internal orthopedic structure, e.g., bone tissue, in the subject. The implant can be controlled to adjust its physical shape, e.g., length, alignment, offset, thickness, radius. Any control of the implant may be performed post-operatively to make adjustments to the implant, or intra-operatively if the surgeon needs to make adjustments to the device during surgery. The orthopedic implant can be used for reconstructive surgery or esthetic surgery to repair damaged bone tissue, or reconstruct or alter the shape of bone tissue. The orthopedic implant can be utilized for implantation and reconstruction into bone tissue including, but not limited to, humerus, radius, ulna, tibia, fibula, femur, glenoid, talus, spine, or any of the metatarsals or metacarpals. The orthopedic implant can include at least one adjustment mechanism configured for securing to at least one orthopedic structure of a subject, and at least one motor operably connected to the at least one adjustment mechanism, wherein the at least one motor is configured to move the at least one adjustment mechanism in at least three degrees of freedom. The at least one adjustment mechanism can be configured to controllably move in at least three degrees of freedom to vary a configuration of an internal orthopedic structure, e.g., bone tissue, in a subject. In an aspect, the orthopedic implant includes the adjustment mechanism that can vary a configuration of an internal orthopedic structure. The implant can include three motors, or in further aspects can include four, five, six or more motors. The implant can include three motors, or in further aspects can include four, five, six or more motors. The implant can include one adjustment mechanism, two opposing adjusting mechanisms, or three opposing adjustment mechanisms. The motors can be configured to move the one adjustment mechanism or two opposing adjustment mechanisms in three degrees of freedom, four degrees of freedom, five degrees of freedom, six degrees of freedom, or more than six degrees of freedom. The motors can be configured to move the three opposing adjustment mechanisms in three degrees of freedom, four degrees of freedom, five degrees of freedom, six degrees of freedom, seven degrees of freedom, eight degrees of freedom, nine degrees of freedom, ten degrees of freedom, eleven degrees of freedom, twelve degrees of freedom, or more than twelve degrees of freedom. The implants can be configured with one or more sensors, controllers, transmitters, or other elements that allow the implant to sense or otherwise detect certain conditions within the orthopedic structure and then perform a predetermined function in response thereto. The implant can include a controller and transmitter configured to receive an input signal to control actuation of at least one of the at least one motors. The implant can further include a sensor configured to inform the controller in response to a sensed condition of the orthopedic structure. The sensors can be configured to detect pressure and/or direction of movement of the orthopedic structure in a manner such that the implant can be controlled to adjust its physical shape in at least three degrees of freedom including translational degrees of freedom and rotational degrees of freedom, e.g., adjustments in length, alignment, offset, thickness, radius. The implant can further include a transmitter in communication with the sensor and the controller, wherein the transmitter is configured to report activity of the implant to an external source. The transmitter, in communication with the sensor and the controller, can be configured to send an actuation signal to the at least one motor.

The orthopedic implant includes at least one motor configured to move at least one adjustment mechanism, wherein the at least one motor can be remotely-actuated in a subject. Remote actuation of the orthopedic implant allows a surgeon to post-operatively or transcutaneously control certain movements of the implant. The surgeon can utilize the remotely-actuated orthopedic implant to control growth and healing of bone tissue in the subject. The orthopedic implant can be controlled by a percutaneous connection or by a wireless signal sent to and from the orthopedic implant.

An orthopedic implant includes at least one adjustment mechanism configured for securing to at least one orthopedic structure of a subject, and at least one motor operably connected to the at least one adjustment mechanism, wherein the at least one motor is configured to move the at least one adjustment mechanism in at least three degrees of freedom. The at least one motor can include at least three motors. The at least one motor can include at least six motors. The at least one motor can be configured to move the at least one adjustment mechanism in six degrees of freedom.

The implant can further include a controller configured to receive an input signal to actuate the at least one motor. The implant can further include a remote source configured to send the input signal. The implant can further include a sensor configured to send the input signal. The implant can further include a computer-readable storage medium configured to send the input signal. The controller can be configured to control actuation of the at least one motor configured to maintain the internal orthopedic structure in a defined position. The controller can be configured to control actuation of the at least one motor to execute a sequence of two or more defined configurational changes to the adjustment mechanism. The controller can be configured to receive the input signal originating from human input. The controller can be configured to receive the input signal originating from data input. The data input can include, but is not limited to, X-ray data, magnetic resonance imaging data, or ultrasound data.

The implant can further include a sensor configured to inform the controller in response to a sensed condition of the orthopedic structure. The sensor can be configured to detect one or more of strain, pressure, motion, stress, load, or position change of the orthopedic structure. The sensor can include, but is not limited to, a strain gauge, accelerometer, piezoelectric film, Hall effect sensor, linear variable displacement transducer (LVDT), differential variable reluctance transducer (DVRT), or reed switch sensor. The sensor can be configured to detect health or integrity of the orthopedic structure. The sensor can be configured to detect ultrasound through the orthopedic structure or conductivity of the orthopedic structure. The sensor can be configured to detect an osteogenic cell marker. The osteogenic cell marker can be on a cell including, but not limited to, a mesenchymal stem cell or osteoblast. The osteogenic cell marker can include, but is not limited to, alkaline phosphatase, osteocalcin, CBFA1/Osf2, or collagen 1A1.

The implant can further include a transmitter in communication with the sensor and the controller, the transmitter configured to report activity of the implant to an external source. The transmitter can be configured to report activity of the implant including the sensed condition of the orthopedic structure. The external source can include, but is not limited to, a human being or computing device. The implant can further include a transmitter in communication with the sensor and the controller, the transmitter configured to send an actuation signal to the at least one motor.

In an aspect, the at least one motor is remotely-actuated. The at least one motor can include, but is not limited to, at least one of an electronic motor, electrostrictive motor, piezoelectric motor, ultrasonically-activated motor, shape memory alloy actuator, paraffin actuator, electromagnetic solenoid, or electroactive polymer. The at least one motor can include, but is not limited to, a stepper motor, drive motor, or servomotor. The at least one motor can further include a piezoelectric stepper motor. The at least one motor can further include an ultrasonic lead screw motor. The piezoelectric motor can be configured to hold a position between activations.

In an aspect, the at least one motor can be configured to controllably move the adjustment mechanism in at least three degrees of freedom to lengthen the internal orthopedic structure, shorten the internal orthopedic structure, tighten the internal orthopedic structure, apply compression to the internal orthopedic structure, twist the internal orthopedic structure, shear the internal orthopedic structure, increase or decrease stress or load on the internal orthopedic structure, or adjust curvature of the internal orthopedic structure. In an aspect, the at least one motor can be configured to controllably move the adjustment mechanism in at least three degrees of freedom including translational movement along one or more of three substantially perpendicular axes or rotational movement about one or more of the three substantially perpendicular axes, to controllably move two or more surfaces of the adjustment mechanism. The at least one motor can be configured to activate the adjustment mechanism to controllably move the two or more surfaces of the adjustment mechanism in at least three degrees of freedom. The two or more surfaces of the adjustment mechanism can be configured to be attached to the orthopedic structure. The adjustment mechanism can be configured to be incrementally adjusted.

In an aspect, the orthopedic structure is bone. The adjustment mechanism can be configured to be attached at a bone fracture site, bone graft, or fused bone. The at least one motor can be powered from a remote energy source including, but not limited to, coupled via conductors, electromagnetic energy, ultrasonic energy, electric energy, or magnetic energy. The at least one motor can be powered from an internal energy source including, but not limited to, battery, capacitor, or mechanical storage.

A method includes providing an orthopedic implant comprising at least one adjustment mechanism configured for securing to at least one orthopedic structure of a subject; and at least one motor operably connected to the at least one adjustment mechanism;, wherein the at least one motor is configured to move the at least one adjustment mechanism in at least three degrees of freedom.

The method can further include providing a controller configured to receive an input signal to actuate the at least one motor. The method can further include providing a remote source configured to send the input signal. The method can further include providing a sensor configured to send the input signal. The method can further include providing a computer-readable storage medium configured to send the input signal. The controller can be configured to control actuation of the at least one motor configured to maintain the internal orthopedic structure in a defined position. The controller can be configured to control actuation of the at least one motor to execute a sequence of two or more defined configurational changes to the adjustment mechanism. The controller can be configured to receive the input signal originating from human input. The controller can be configured to receive the input signal originating from data input. The data input can include, but is not limited to, X-ray data, magnetic resonance imaging data, or ultrasound data.

The method can further include providing a sensor configured to inform the controller in response to a sensed condition of the orthopedic structure. The sensor can be configured to detect one or more of strain, pressure, motion, stress, load, or position change of the orthopedic structure. The sensor can include, but is not limited to, a strain gauge, accelerometer, piezoelectric film, Hall effect sensor, linear variable displacement transducer (LVDT), differential variable reluctance transducer (DVRT), or reed switch sensor. The sensor can be configured to detect health or integrity of the orthopedic structure. The sensor can be configured to detect ultrasound through the orthopedic structure or conductivity of the orthopedic structure. The sensor can be configured to detect an osteogenic cell marker. The osteogenic cell marker can be on a cell including, but not limited to, a mesenchymal stem cell or osteoblast. The osteogenic cell marker can include, but is not limited to, alkaline phosphatase, osteocalcin, CBFA1/Osf2, or collagen 1A1.

The method can further include providing a transmitter in communication with the sensor and the controller, the transmitter configured to report activity of the implant to an external source. The transmitter can be configured to report activity of the implant including the sensed condition of the orthopedic structure. The external source can include, but is not limited to, a human being or computing device. The implant can further include a transmitter in communication with the sensor and the controller, the transmitter configured to send an actuation signal to the at least one motor.

In an aspect, the at least one motor is remotely-actuated. The at least one motor can include, but is not limited to, at least one of an electronic motor, electrostrictive motor, piezoelectric motor, ultrasonically-activated motor, shape memory alloy actuator, paraffin actuator, electromagnetic solenoid, or electroactive polymer. The at least one motor can include, but is not limited to, a stepper motor, drive motor, or servomotor. The at least one motor can further include a piezoelectric stepper motor. The at least one motor can further include an ultrasonic lead screw motor. The piezoelectric motor can be configured to hold a position between activations.

In an aspect, the at least one motor can be configured to controllably move the adjustment mechanism in at least three degrees of freedom to lengthen the internal orthopedic structure, shorten the internal orthopedic structure, tighten the internal orthopedic structure, apply compression to the internal orthopedic structure, twist the internal orthopedic structure, shear the internal orthopedic structure, increase or decrease stress or load on the internal orthopedic structure, or adjust curvature of the internal orthopedic structure. In an aspect, the at least one motor can be configured to controllably move the adjustment mechanism in at least three degrees of freedom including translational movement along one or more of three substantially perpendicular axes or rotational movement about one or more of the three substantially perpendicular axes, to controllably move two or more surfaces of the adjustment mechanism. The at least one motor can be configured to activate the adjustment mechanism to controllably move the two or more surfaces of the adjustment mechanism in at least three degrees of freedom. The two or more surfaces of the adjustment mechanism can be configured to be attached to the orthopedic structure. The adjustment mechanism can be configured to be incrementally adjusted.

In an aspect, the orthopedic structure is bone. The adjustment mechanism can be configured to be attached at a bone fracture site, bone graft, or fused bone. The at least one motor can be powered from a remote energy source including, but not limited to, coupled via conductors, electromagnetic energy, ultrasonic energy, electric energy, or magnetic energy. The at least one motor can be powered from an internal energy source including, but not limited to, battery, capacitor, or mechanical storage.

A system includes an orthopedic implant comprising at least one adjustment mechanism configured for securing to at least one orthopedic structure of a subject; and at least one motor operably connected to the at least one adjustment mechanism, wherein the at least one motor is configured to move the at least one adjustment mechanism in at least three degrees of freedom. The at least one motor can include at least three motors. The at least one motor can include at least six motors. The at least one motor can be configured to move the at least one adjustment mechanism in six degrees of freedom.

The system can further include a controller configured to receive an input signal to actuate the at least one motor. The system can further include a remote source configured to send the input signal. The system can further include a sensor configured to send the input signal. The system can further include a sensor configured to inform the controller in response to a sensed condition of the orthopedic structure. The sensor can be configured to detect one or more of strain, pressure, motion, stress, load, or position change of the orthopedic structure.

A device includes a system including a signal bearing medium including one or more instructions for providing an orthopedic implant comprising at least one adjustment mechanism configured for securing to at least one orthopedic structure of a subject; and at least one motor operably connected to the at least one adjustment mechanism, wherein the at least one motor is configured to move the at least one adjustment mechanism in at least three degrees of freedom. The at least one motor can include at least three motors. The at least one motor can include at least six motors. The at least one motor can be configured to move the at least one adjustment mechanism in six degrees of freedom.

The device can further include a controller configured to receive an input signal to actuate the at least one motor. The device can further include a remote source configured to send the input signal. The device can further include a sensor configured to send the input signal. The device can further include a sensor configured to inform the controller in response to a sensed condition of the orthopedic structure. The sensor can be configured to detect one or more of strain, pressure, motion, stress, load, or position change of the orthopedic structure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
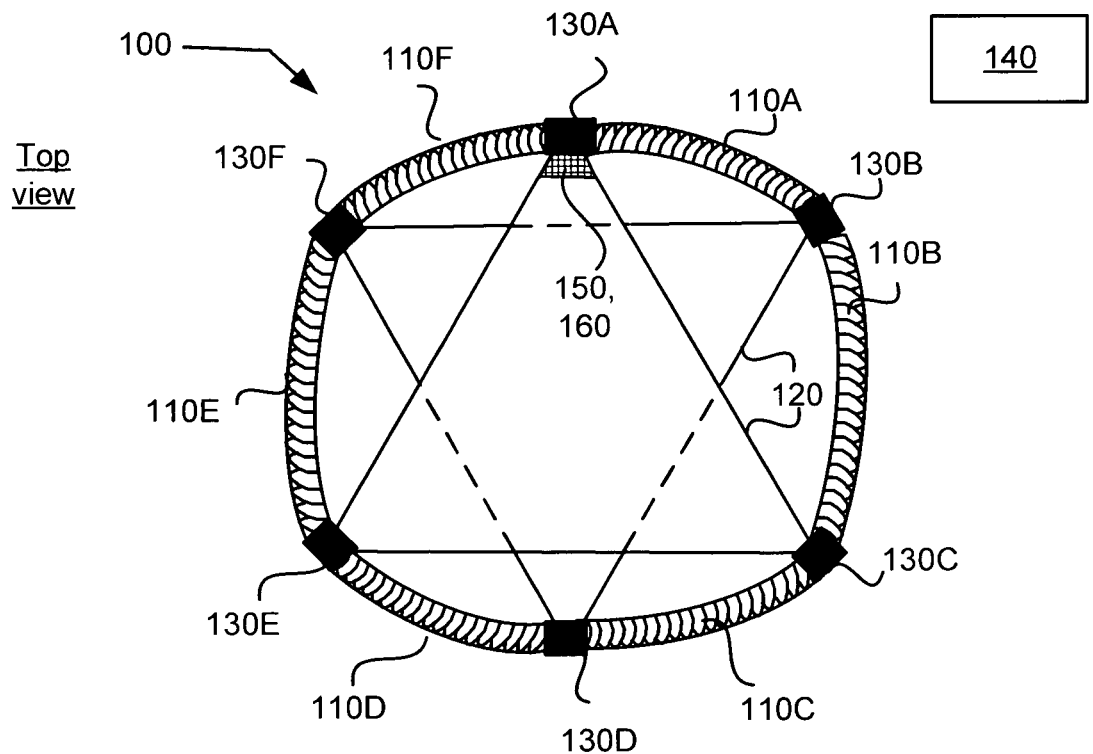
FIGS. 1A, 1B, and 1C depict a diagrammatic view of an aspect of an embodiment of an orthopedic implant.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

An orthopedic implant described herein allows a surgeon to control certain movements of at least a portion of the implant in multiple degrees of freedom during surgery or post-operatively. Post-operatively, the surgeon may transcutaneously control the orthopedic implant to vary a configuration of an internal orthopedic structure in the subject. The surgeon may utilize the orthopedic implant to control growth and healing of the internal orthopedic structure, e.g., bone tissue, in the subject. The implant can be controlled to adjust its physical shape, e.g., length, alignment, offset, thickness, radius. Any control of the implant may be performed post-operatively to make adjustments to the implant, or intra-operatively if the surgeon needs to make adjustments to the device during surgery. The orthopedic implant can be used for reconstructive surgery or esthetic surgery to repair damaged bone tissue, or reconstruct or alter the shape of bone tissue. The orthopedic implant can be utilized for implantation and reconstruction into bone tissue including, but not limited to, humerus, radius, ulna, tibia, fibula, femur, glenoid, talus, spine, or any of the metatarsals or metacarpals. The orthopedic implant can include at least one adjustment mechanism configured for securing to at least one orthopedic structure of a subject, and at least one motor operably connected to the at least one adjustment mechanism, wherein the at least one motor is configured to move the at least one adjustment mechanism in at least three degrees of freedom. The at least one adjustment mechanism can be configured to controllably move in at least three degrees of freedom to vary a configuration of an internal orthopedic structure, e.g., bone tissue, in a subject. In an aspect, the orthopedic implant includes the adjustment mechanism that can vary a configuration of an internal orthopedic structure. The implant can include three motors, or in further aspects can include four, five, six or more motors. The implant can include one adjustment mechanism, two opposing adjusting mechanisms, or three opposing adjustment mechanisms. The motors can be configured to move the one adjustment mechanism or two opposing adjustment mechanisms in three degrees of freedom, four degrees of freedom, five degrees of freedom, six degrees of freedom, or more than six degrees of freedom. The motors can be configured to move the three opposing adjustment mechanisms in three degrees of freedom, four degrees of freedom, five degrees of freedom, six degrees of freedom, seven degrees of freedom, eight degrees of freedom, nine degrees of freedom, ten degrees of freedom, eleven degrees of freedom, twelve degrees of freedom, or more than twelve degrees of freedom. The implants can be configured with one or more sensors, controllers, transmitters, or other elements that allow the implant to sense or otherwise detect certain conditions within the orthopedic structure and then perform a predetermined function in response thereto. The implant can include a controller and transmitter configured to receive an input signal to control actuation of at least one of the at least one motors. The implant can further include a sensor configured to inform the controller in response to a sensed condition of the orthopedic structure. The sensors can be configured to detect pressure and/or direction of movement of the orthopedic structure in a manner such that the implant can be controlled to adjust its physical shape in at least three degrees of freedom including translational degrees of freedom and rotational degrees of freedom, e.g., adjustments in length, alignment, offset, thickness, radius. The at least one motor can be configured to move the at least one adjustment mechanism, in at least three degrees of freedom. The at least one motor can be geared to move in one degree, two degrees, or three degrees of freedom, including up to six or more degrees of freedom. The at least one motor can be geared utilizing a geared transmission and/or a hinged universal-type joint to move in at least one degree of freedom. The implant can further include a transmitter in communication with the sensor and the controller, wherein the transmitter is configured to report activity of the implant to an external source. The transmitter, in communication with the sensor and the controller, can be configured to send an actuation signal to the at least one motor.

The orthopedic implant includes at least one motor configured to move at least one adjustment mechanism, wherein the at least one motor can be remotely-actuated in a subject. The at least one motor can be configured to move the at least one adjustment mechanism, in at least three degrees of freedom. Remote actuation of the orthopedic implant allows a surgeon to post-operatively or transcutaneously control certain movements of the implant. The surgeon can utilize the remotely-actuated orthopedic implant to control growth and healing of bone tissue in the subject. The orthopedic implant can be controlled by a percutaneous connection or by a wireless signal sent to and from the orthopedic implant.

Aspects of the orthopedic implant include at least one motor configured to move at least one adjustment mechanism that can provide distraction forces to, for example, relieve pressure on certain orthopedic structures, for example, compression forces to fix or stabilize motion across structures, for example, shock absorbing qualities to help relieve load from certain orthopedic structures, and, for example, therapeutic activity to reduce or eliminate an orthopedic condition or symptoms thereof, e.g., to reduce inflammation and pain in the subject. The at least one motor can be configured to controllably move or move the adjustment mechanism in at least three degrees of freedom to lengthen the internal orthopedic structure, shorten the internal orthopedic structure, tighten the internal orthopedic structure, apply compression to the internal orthopedic structure, twist the internal orthopedic structure, shear the internal orthopedic structure, increase or decrease stress or load on the internal orthopedic structure, or adjust curvature of the internal orthopedic structure.

A sensor can be secured on the adjustment mechanism of the orthopedic implant. The sensor can be embedded in a position on the internal orthopedic structure in a subject. The sensor can sense stress on the adjustment mechanism from orthopedic structures secured to it, or can sense other information that can be desirable to monitor. The sensor can be configured to inform the controller in response to a sensed change in the internal orthopedic structure, e.g., bone tissue. The controller can be configured to receive a remote signal to control actuation of at least one of the at least one motors wherein the motors can move the at least one adjustment mechanism. The controller can communicate sensed information via a transmitter to report activity of the implant to an external source, e.g., when interrogated. In an aspect, the orthopedic implant can include a distraction rod in which distracting element comprises two opposing rods with abutting ends and an adjusting device connecting the threaded abutting ends. The distraction rod can be extendable after implanted to slowly distract the joint until a desired result, e.g., reduction of patient pain or discomfort, is achieved or degree of release of stress on a joint is achieved. This can be visually determined, determined according to patient feedback or determined by a sensor positioned on or adjacent the implanted distraction system. The sensor can be near the attachment site to the bone. The sensor can be configured to detect one or more of strain, pressure, motion, stress, load, or position change of the orthopedic structure. The sensor can be a strain gauge, accelerometer, piezoelectric film, Hall effect sensor, linear variable displacement transducer (LVDT), differential variable reluctance transducer (DVRT), or reed switch sensor, or other sensor that can be used, positioned or configured to determine a mechanical load on the orthopedic implant or distraction device. The sensor can also be a stand alone sensor positioned in or adjacent a distracted joint and configured to sense a parameter indicative of forces at the joint. The sensor can include an electronic circuit that is configured to telemetrically send a signal containing information correlated to such sensed forces.

A responsive orthopedic implant is described in which an on-board sensor, or multiple sensors, and at least one motor configured to move at least one adjustment mechanism, are used in combination. The sensor monitors some physical, chemical, or other parameter(s). The sensor can be configured to detect one or more of strain, pressure, motion, stress, load, or position change of the orthopedic structure When the sensor detects some absolute or relative change in such a parameter(s), the orthopedic implant responds by initiating some desirable adjustment through actuation of the at least one motor. During such actuation, the sensor can continue to monitor the parameter(s). Actuation is terminated when the sensor detects that the parameter(s) has returned to within predetermined limits.

The orthopedic implant can be a passively powered from an external power source where the external device can interrogate the sensor for information. The at least one motor can be powered from a remote energy source coupled via conductors, electromagnetic energy, ultrasonic energy, electric energy, or magnetic energy. In another aspect, the at least one motor can be powered from an internal energy source including battery, capacitor, or mechanical storage. The electronic circuit can also include signal processing circuits or memory. A remotely actuatable length adjusting motor can include the adjustment mechanism, e.g., distraction rod. A mechanical, magnetic or other adjusting device such as a motor, e.g., electronic motor, electrostrictive motor, piezoelectric motor, ultrasonically-activated motor, shape memory alloy actuator, paraffin actuator, electromagnetic solenoid, or electroactive polymer, can move the distraction rod to adjust the degree of distraction. The motor may be actuatable by the patient or provider or can automatically adjust, can be adjusted by circuit (that can be telemetrically controlled and/or powered), or can adjust the distraction on demand based at least in part on information sensed by the sensor via control signal through electronic circuit. The distraction rod can also include a predetermined mechanism that is designed to break or fail when a certain force is applied to the device. The device can be configured to release, disengage, fail or break with application of a predetermined or selected force by creating a release mechanism or faults in the material or selecting material or structure specifications. For example, the device can be constructed to operate under given normal operating forces but to release, disengage, fail or break prior to a force sufficient to fracture the bone.

An orthopedic implant is described herein for use in a method for treating an orthopedic condition, e.g., for internal fixation of a fractured bone or for osteotomy. The method includes providing an orthopedic implant configured to attach to an internal orthopedic structure, e.g., fractured bone, of the subject. The orthopedic implant can include at least one adjustment mechanism configured for securing to at least one orthopedic structure of a subject, and at least one motor operably connected to the at least one adjustment mechanism, wherein the at least one motor is configured to move the at least one adjustment mechanism in at least three degrees of freedom. The orthopedic implant can be used to reduce or eliminate the orthopedic condition or symptoms of the orthopedic condition, for example, to promote healing of the fractured bone. Internal fixation can be used to achieve prompt and if possible full function of a fractured limb, with rapid rehabilitation.

An orthopedic implant including at least one adjustment mechanism configured for securing to at least one orthopedic structure of a subject, and at least one motor operably connected to the at least one adjustment mechanism used for fracture fixation of the at least one orthopedic structure can include the at least one adjustment mechanism in one or more categories including, but not limited to, wires, pins and screws, plates, and intramedullary nails or rods. Staples and clamps can also be used for osteotomy or fracture fixation of the at least one orthopedic structure. See, e.g., Hunter, et al., *RadioGraphics* 23:195-213, 2003; Taljanovic, et al., *RadioGraphics* 23:1569-1590, 2003; Taljanovic, et al., *RadioGraphics* 25:859-870, 2005, each of which is incorporated herein by reference. The orthopedic implant can have at least one adjustment mechanism including one or more pins to attach to the internal orthopedic structure of the subject. Pins can be used to hold pieces of bone together and can be used under conditions in which the bone pieces or fragments are too small to be fixed with screws. Pins can be removed after a certain period of time or can be left permanently. Fixation pins can be smooth or threaded and of varying sizes. Examples of fixation pins include, but are not limited to, Kirschner (K) wires and Steinman pins. These devices are used for temporary fixation of the fracture fragments during fracture reduction, to attach skeletal traction devices, and as guides for the accurate placement of larger cannulated screws. Pins can also be used for definitive fracture treatment. The orthopedic implant can include other types of pins including, but not limited to, Hagie pins, partially threaded orthopedic fixation pins designed for hip fractures; Knowles pins, percutaneous pins; and Rush pins, orthopedic fixation pins with sled-runner tip and hooked ends.

The orthopedic implant can have at least one adjustment mechanism including one or more wires to attach to the internal orthopedic structure of the subject. Wires can be used as sutures or threads to "sew" the fractured bones back together. Wire can be used alone or in combination with other orthopedic implant devices. The wire can be of various diameters and can be smooth or braided. Wires are frequently used to reattach osteotomized bone fragments. In combination with pins or screws, the wires can be used to create a tension band, that uses distractive muscular forces to create compression at the fracture site. Circumferential cerclage wires are commonly used in conjunction with intramedullary fixation to stabilize long bone fragments. Wire can be used alone to treat fractures of small bones, such as those found in the hand or foot. Kirschner wire (K wire) is a common wire type used for fixation of fracture fragments during fracture reduction and skeletal traction. Tension band wiring is a type of orthopedic wiring used to absorb tension and apply compression to bony fragments at a fracture site.

The orthopedic implant can have at least one adjustment mechanism including one or more fixation screws. The adjustment mechanism is configured to controllably move in at least three degrees of freedom to vary a configuration of the internal orthopedic structure, e.g., bone fracture, in the subject. Fixation screws or bone screws are any type of screw used to pull together two pieces of bone or to attach a plate, rod or nail to a bone. Screws can be used alone to hold a fracture or in combination with plates, rod or nails. The screw can include a screw head, which is the bulbous portion of the screw engaged by the screwdriver, and the shank or core, that can be variable in length and diameter and can be partially or fully threaded. Screws can be further self-tapping (with cutting edges) or non-self-tapping. Screws can further include a standard point or a trocar point. Screws are commonly used in combination with plates and nails or rods. Screws can be cortical or cancellous. Cortical screws are fully threaded, usually have a smaller thread diameter and pitch, and are designed to be used in the diaphysis or mid section of a bone. Cancellous screws have deeper threads, larger thread diameter, and greater pitch relative to cortical screws and are commonly used to cross long segments of cancellous bone. Screws that cross the fracture line are termed interfragmentary screws and provide compression between the fracture fragments to enhance fracture stability and promote healing. Other types of screws include, but are not limited to, compression screws, cortical bone screws, dynamic hip screws, dynamic compression screws, Herbert screws, interfragmentary (lag) screws, interlocking screws, Kurosaka screws, lag screws, malleolar bone screws, syndesmotic screws, cannulated screws, or interference screws.

The orthopedic implant can have at least one adjustment mechanism including one or more plates. Plates constitute internal splints that hold the fractured ends of bone together. One or more plates can be extended along the fractured bone and screwed into place and can be removed after healing or left in place. The plates commonly include on or more holes through which screws, rods or nails can be inserted. The number and position of the holes in a plate creates potential flex points in the otherwise rigid plate. Plates can be used for both rigid and flexible fracture fixation. With flexible fixation, the fracture fragments displace in relation to each other when the load is applied across the fracture site. Fracture fixation is considered flexible if it allows appreciable interfragmentary movement under functional load. Fracture plating can involve compression plating or neutralization plating. Compression plating applies compression to the fractured ends. Dynamic compression plate is an orthopedic fracture fixation plate with oval holes designed to provide compression of the fracture as eccentrically placed screws are tightened on either side of the fracture line. Dynamic compression plates are designed to compress fracture fragments together rather then merely hold them in contact. They are typically used for fractures that are stable. Neutralization plating involves using an orthopedic fixation plate with interfragmentary screws to protect the screw fixation by neutralizing various mechanical stresses at the fracture site. Neutralization plates are typically used in the shaft of long bones. Other types of plates can be used including, but not limited to, reconstruction plates that are notched between the holes, allowing the plates to be bent or contoured in three planes and commonly used to accommodate the complex anatomy of pelvic fractures; buttress plates, typically used in metaphyseal regions, such as the distal portion of the radius or the proximal portion of the tibia; Holt nail plates, fixed angle nail-plates used to treat hip fractures; Moe plates, metallic bone plates used for fixation of an intertrochanteric femur fracture; Morscher plates, anterior cervical spine fixation system using a plate an a hollow screw; Orion plates, a type of anterior cervical spine fusion plate; posterior cervical plates for fixation of unstable spine fractures and dislocations or to stabilize the spine after surgery; Sherman plates; or tubular plates, fracture fixation plates with a circular profile that are thin, self-compressing, and easily bent to adapt to varying fracture conditions.

The orthopedic implant can have at least one adjustment mechanism including one or more nails or rods. Nails and rods can be used to generally align bones such as the long bones of the leg. A nail or rod can be inserted through the hollow end or medullary space of the bone that normally contains the marrow. Screws can be used to hold the nail or rod in place and can be inserted in the proximal and distal bone to fix the nail or rod in place and to provide control of rotational and compressive forces. Intramedullary nailing is the standard treatment for diaphyseal fractures of the femur and tibia. Intramedullary rods are also used for fracture fixation of long bones. Examples of nails include, but are not limited to, Enders nails, Gross-Kempfe interlocking nails, Hansen-Street nails, Kuntscher nails (intramedullary nail), Lottes nails, Massie nails (telescoping nail-plate assembly used to treat intertrochanteric hip fractures), McGlaughlin nails, Neufeld nails, Sage nails (intramedullary fixation of the radius and ulna), Sampson nails (hollow cylindrical rod with multiple external flutes), Schneider nails (four-flanged intramedullary nails used for femoral shaft fractures), Smith-Peterson nails (flanged nails for treating fractures of the femoral neck), or triflanged nails (fixation nails used for intracapsular hip fractures). Examples of rods include, but are not limited to, Knodt rods (orthopedice fixation rods used for spine reconstruction), or reconstruction rods (used to treat fractures of the femoral neck, intertrochanteric, or subtrochanteric areas), In an aspect, the orthopedic implant can have at least one adjustment mechanism including a combination of one or more of screws, plates, pins, nails, and/or rods. This is particularly the case in orthopedic implants designed to stabilize the spinal cord. Posterior spinal instrumentation or fixation is a generic term used for a wide variety of wires, rods, plates, and screws designed for thoracic or lumbar spine stabilization after surgery to correct severe traumatic, congenital, or developmental spinal abnormalities. There are many different posterior spinal instrumentation designs, including, but not limited to, Luque and Hartshill rectangles; Harrington and Knodt rods; Steffee, Edwards, Roy Camille, Texas Scottish Rite Hospital (TSRH), or Cotrell-Dubousset pedicle fixation systems. For example, the Cotrell-Dubousset system is a complex orthopedic system of rods, hooks, cross-links, and screws for the posterior fixation of the spine. Alternatively, the orthopedic implant can be used in a method for treatment of spinal injury. The orthopedic implant can be one or more anterior cervical plates, a system of plates and screws placed anteriorly in the spine for fixation of unstable spine fractures and dislocations, or for stabilization of the spine after surgery. Other examples of orthopedic implants used for spine stabilization include, but are not limited to, the Dwyer-Zielke system, a complex orthopedic spine-fixation system used for correcting thoracolumbar scolioisis in which a unilateral plate is affixed to the lateral portion of adjacent vertebral bodies by screws; Kaneda device, a spinal fixation device designed to facilitate one-stage treatment of thoracolumbar lesions; the modular spine-fixation system, a spine fixation system using pedicle screws, distraction hooks, intermediate screws, and a universal rod; or the Wiltse system, an orthopedic spine-fixation system in which pedicle screws are connected to a rod by clamps. Other combination systems have been described for treating the long bones, e.g., sliding nail plate device used to treat femoral neck and intertrochanteric fractures. The orthopedic device has at least one adjustment mechanism including a side plate and a tunnel through which a lag screw or pins can glide to compensate for impaction at the fracture site and a Zickle device used to stabilize pathologic femur fractures and subtrochanteric hip fractures and includes an intramedullary rod and triflanged femoral neck nail combination. A combination of titanium mini plates, screws and wires can be used for repairing broken bones during facial reconstruction and can be done in combination with bone grafts and/or synthetic bone material.

The orthopedic implant can be used for arthroplasty of a damaged joint. Arthroplasty is an operative procedure of orthopedic surgery performed to restore joint function, in which an arthritic or destructive or necrotic joint or dysfunctional joint surface is replaced with something better or by remodeling or realigning the joint by osteotomy or some other procedure. In many cases, a prosthetic implant is used to totally or partially replace the native joint. A total arthroplasty involves prosthetic replacement of both sides of a joint, whereas a hemi-arthroplasty involves replacement of only one side of a joint, such as a hip bipolar prosthesis. In an aspect, a hip joint that is affected by osteoarthritis can be replaced entirely (total hip arthroplasty) with a prosthetic hip. Both the acetabulum (hip socket) and the head and neck of the femur are replaced with interacting prosthetic implants. The purpose of this procedure is to relieve pain, to restore range of motion and to improve walking ability, leading to the improvement of muscle strength. Other forms of arthroplasty include interpositional arthroplasty with interposition of some other tissue like skin, muscle or tendon to keep inflammatory surfaces apart or excisional arthroplasty in which the joint surface and bone are removed leaving scar tissue to fill in the gap. Other forms of arthroplasty include, but are not limited to, resectional arthroplasty, resurfacing arthroplasty, mold arthroplasty, cup arthroplasty, or silicone replacement arthroplasty. See, e.g., Taljanovic, et al., *RadioGraphic* 23:1295-1314, 2003, which is incorporated herein by reference.

The orthopedic implant can have at least one adjustment mechanism including a prosthesis that totally or partially replaces the shoulder joint. Arthroplasty of the shoulder is indicated for degenerative and inflammatory arthritis refractory to medical therapy, osteonecrosis, and proximal humerus fractures. In this instance, the humeral component of the orthopedic implant can include a metallic stem component anchored with or without cement in the proximal humerus and a modular humeral head that articulates with either the native glenoid (socket) in the shoulder blade (hemiarthroplasty) or with a prosthetic polyethylene or metal glenoid (total shoulder arthroplasty). The glenoid prosthesis can be attached to the shoulder blade using cement (polyethylene) or screws (metal).

The orthopedic implant can have at least one adjustment mechanism including a prosthesis that totally or partially replaces the elbow joint. Arthroplasty of the elbow is indicated for advanced inflammatory or degenerative arthritis refractory to medical therapy and complex fractures or nonunion of the distal humerus. Several types of elbow arthroplasty are currently performed, e.g., unconstrained or resurfacing elbow arthroplasty, semiconstrained elbow arthroplasty, and constrained elbow arthroplasty. The unconstrained elbow prosthesis consists of two separate humeral and ulnar metal components that articulate by a high-density polyethylene component. Constrained elbow prostheses consist of rigid hinges and are constructed with either metal-on-metal or metal-to-high density polyethylene parts connected through a bushing, or a separate polyethylene piece that links the humeral and ulnar components. In placement of a constrained prosthesis, the radial head is resected proximal to the annular ligament. A semiconstrained total elbow arthroplasty prosthesis is exemplified by the DISCOVERY® elbow prosthesis (Biomet, Warsaw, Ind.).

The orthopedic implant can have at least one adjustment mechanism including a prosthesis that totally or partially replaces the joints within the wrist. The implant can facilitate various degrees of motion of the wrist joint and can be a ball and socket design, a cementless captured ball design, or a semiconstrained, transversely oriented, ellipsoid design. The latter is exemplified by the UNIVERSAL II® total wrist prosthesis which is composed of a flat distal component with a prong that is cemented into the capitate and with radial and ulnar screws placed through the prosthesis and into the peripheral carpal bones. A polyethylene insert is placed between the cemented titanium components. See Taljanovic et al., *RadioGraphics* 23:1295-1314, 2003, which is incorporated herein by reference.

An orthopedic implant can be used to replace metacarpophalangeal (MCP) or interphalangeal joints in the hand. An example is the Swanson MCP implant, a silicone prosthesis with circumferential titanium grommets. Alternatively, the articular cartilage of the MCP joint can be replaced with a prosthetic cap.

The orthopedic implant can have at least one adjustment mechanism including a prosthesis that totally or partially replaces the hip joint. Arthroplasty of the hip is indicated for disabling pain secondary to severe osteoarthritis, avascular necrosis, ankylosis secondary to prior infection or surgery, tumors around the hip joint, and hip fractures. A total or partial hip replacement is a surgical procedure whereby the diseased cartilage and bone of the hip joint is surgically replaced with artificial materials. The normal hip joint is a ball and socket joint. The socket is a "cup-shaped" bone of the pelvis called the acetabulum. The ball is the head of the thigh bone (femur). Total or partial hip joint replacement involves surgical removal of the diseased ball and/or socket and replacing them with a metal ball and stem inserted into the femur bone and an artificial plastic cup socket. Hip arthroplasty can be one of several types. A unipolar hip hemiarthroplasty (endoprosthesis) is a single metallic orthopedic implant inserted into the femur with the prosthetic head sized appropriately to press fit into the patient's acetabulum. A bipolar hip hemiarthroplasty uses an orthopedic implant comprised of two components that snap together to form one articular unit and includes a stem inserted into the femur with a small diameter head and a separate acetabular component made of metal shell lined with polyethylene. A total hip arthroplasty also uses an orthopedic implant comprised of two components: a stemmed femoral component with a prosthetic femoral head and an acetabular component. The device can be modular with separate femoral stem, head, acetabular shell, and acetabular liner in varying sizes to generate custom prosthesis for any given patient. The one or more components can be cemented with a bone cement such as methylmethacrylate. Alternatively, a cementless fixation can be used based on a rough or porous surface that allows bony ingrowth from the normal femur into the prosthesis stem. The components of the orthopedic implant can be additionally fixed with screws or wires The orthopedic implant can have at least one adjustment mechanism including a prosthesis that totally or partially replaces the knee joint. Arthroplasty of the knee is indicated for advanced degenerative and refractory inflammatory arthritis. Arthroplasty of the knee can be unicompartmental arthroplasty in which either the inside (medial) or outside (lateral) compartments of the knee are replaced. Alternatively, arthroplasty of the knee can involve total knee replacement in which the femoral, tibial, and patellar articular surfaces are all resurfaced using metal and polyethylene bearing surfaces. During a total knee replacement, the end of the femur bone is removed and replaced with a metal shell. The end of the tibia is also removed and replaced with a channeled plastic piece with a metal stem. The femoral and tibial components can be stemmed, cemented, noncemented, anchored with screws, or a combination thereof. Depending on the condition of the kneecap portion of the knee joint, a plastic "button" can also be added under the kneecap surface. The posterior cruciate ligament is a tissue that normally stabilizes each side of the knee joint so that the lower leg cannot slide backward in relation to the thigh bone. In total knee replacement surgery, this ligament is either retained, sacrificed, or substituted by a polyethylene post. Examples of total knee replacement prostheses include, but are not limited to, unicompartmental knee prosthesis (e.g., Johnson & Johnson; Rayham, Mass.), cruciate-retaining total knee prosthesis (e.g., NATURAL-KNEE II® knee prosthesis system; Zimmer, Inc.; Warsaw, Ind.), or cruciate-substituting total knee prosthesis (e.g., GENESIS II TOTAL KNEE® knee prosthesis system; Smith & Nephew; London, UK)

The orthopedic implant can have at least one adjustment mechanism including a prosthesis that totally or partially replaces the ankle joint. Arthroplasty of the ankle can be indicated for osteoarthritis and refractory inflammatory arthritis. Prostheses for total ankle replacement include fixed-bearing designs with fully conforming joints and mobile-bearing designs with two articulations and can be either cemented or noncemented. Ankle prostheses are exemplified by the Scandinavian total ankle replacement (STAR), the Buechel-Pappas total ankle arthroplasty (Endotec, South Orange, N.J.), the TNK ankle (Nara, Japan), and the Agility total ankle system (DePuy, Warsaw, Ind.). The STAR device, for example, has three parts: two metal bearing surfaces (cobalt-chromium alloy) plates with bars that fit into the bone and one plastic (polyethylene) spacer that moves between the metal plates like a ball bearing.

The orthopedic implant can have at least one adjustment mechanism including a prosthesis that totally or partially replaces the temporomandibular joint (TMJ). The joint is composed of two bones: the upper temporal bone which is part of the cranium and the lower mandible bone. Arthroplasty of the TMJ can be indicated for refractory inflammatory or autoimmune disease, cancer, or trauma. An orthopedic device for total arthroplasty of the TMJ is exemplified by the Biomet Microfixation TMJ Replacement System (Biomet Microfixation; Jacksonville, Fla.) which includes a condyle (mandibular) implant made of metal cobalt-chromium-molybdenum alloy with a roughened titanium porous coating, a fossa implant made of hard, plastic polyethylene, and titanium allow screws for attaching the condyle and fossa implants to the bone.

In an aspect, the orthopedic implant can be used in conjunction with osteotomy, a surgical operation whereby a bone is cut to shorten, lengthen, or change its alignment. The orthopedic implant can include at least one motor configured to move at least one adjustment mechanism, wherein the adjustment mechanism is configured to controllably move in at least three degrees of freedom to vary a configuration of an internal orthopedic structure in a subject. An orthopedic implant can be used in conjunction with osteotomy to straighten a bone that has healed crookedly following a fracture. Alternatively, orthopedic implant can be used in conjunction with osteotomy to induce bone lengthening, particularly in the legs, and can be performed to normalize a congenital discrepancy in the length of one leg relative to the other. One method is intramedullary distraction in which the leg bone is cut and the two ends fixed together with locking screws. The device slowly forces the two parts of bone apart from one another, allowing new bone formation to fill the gap and eventually lengthen the bone.

The orthopedic implant can be used for arthrodesis, also known as artificial ankylosis or syndesis. Arthrodesis is the artificial induction of joint ossification between two bones via surgery. This procedure is performed to relieve intractable pain in a joint that cannot be managed by pain medication, splints, or other treatment options. The typical causes of such pain are fractures and arthritis. Arthrodesis is most commonly performed on joints in the spine, hand, ankle, and foot. One or more of a combination of nails, rods, pins, screws, and plates can be used to immobilize the joint and can be done in conjunction with a bone graft or synthetic bone substitute to induce bone fusion. For example, small Herbert screws can be used for bone fusion of proximal interphalangeal joints by transfixing the joints. See, e.g., Taljanovic, et al., *RadioGraphics* 25:859-870, 2005, which is incorporated herein by reference. In another aspect, a plate and screw orthopedic device can be used for anterior cervical spine fusion with a cage device filled with bone allograft. Medtronic Sofamor Danek, Memphis, Tenn.; see, e.g., Talianovic, et al., *RadioGraphics* 25: 1119-1132, 2005, which is incorporated herein by reference.

One or more components of the orthopedic implant can be constructed with any of a number of biocompatible materials including, but not limited to, artificial joint surfaces composed of inorganic compounds that include silicates, metallic oxides, carbides, and various refractory hydrides, sulfides, and nitrides; ceramics; alloys that include platinum metals platinum, ruthenium, rhodium, palladium, osmium, and/or iridium; polymers that include polyethylene and poly(methyl methacrylate; PMMA); shape memory alloys, any of a number of shape memory alloys that permit design of implants that can be changed to a desirable body form by a well-controlled heating process; TEFLON; tantalum, a noncorrosive, malleable metal; stainless steel; titanium; or high-strength metal alloys such as forged cobalt-chromium alloy, titanium-6-aluminum-4-vanadium, and high-strength stainless steel.

With reference to the figures, and with reference now to FIGS. 1, 2, 3, 4, 5 and 6 depicted is an aspect of a device or method that can serve as an illustrative environment of and/or for subject matter technologies, for example, an orthopedic implant that can include at least one adjustment mechanism configured for securing to at least one orthopedic structure of a subject, and at least one motor operably connected to the at least one adjustment mechanism, wherein the at least one motor is configured to move the at least one adjustment mechanism in at least three degrees of freedom. In an aspect, the adjustment mechanism is configured to controllably move the orthopedic structure of the subject in six degrees of freedom. The specific devices and methods described herein are intended as merely illustrative of their more general counterparts.

Figure 1B:
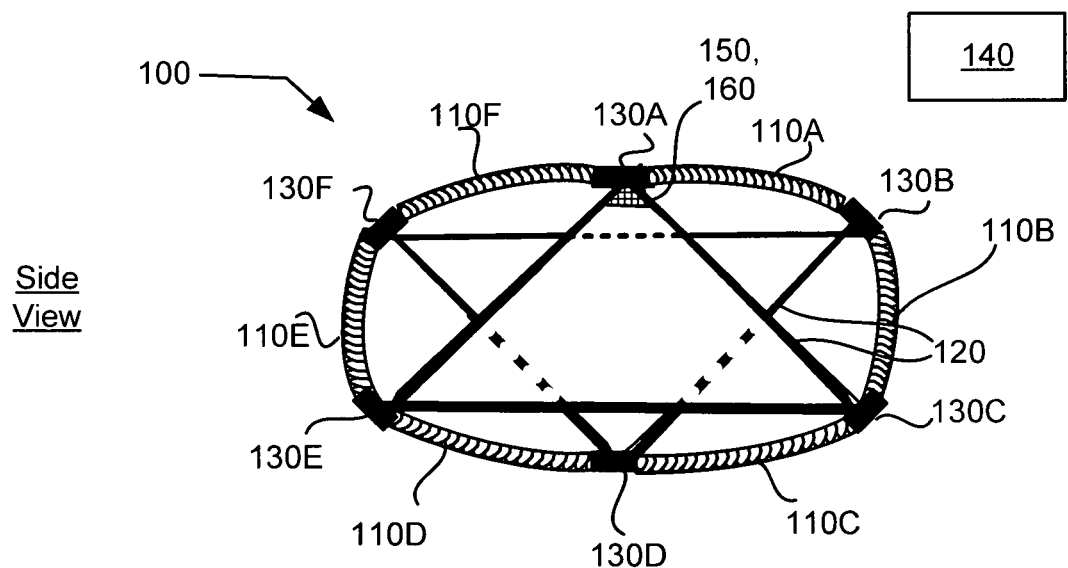
Figure 1C:
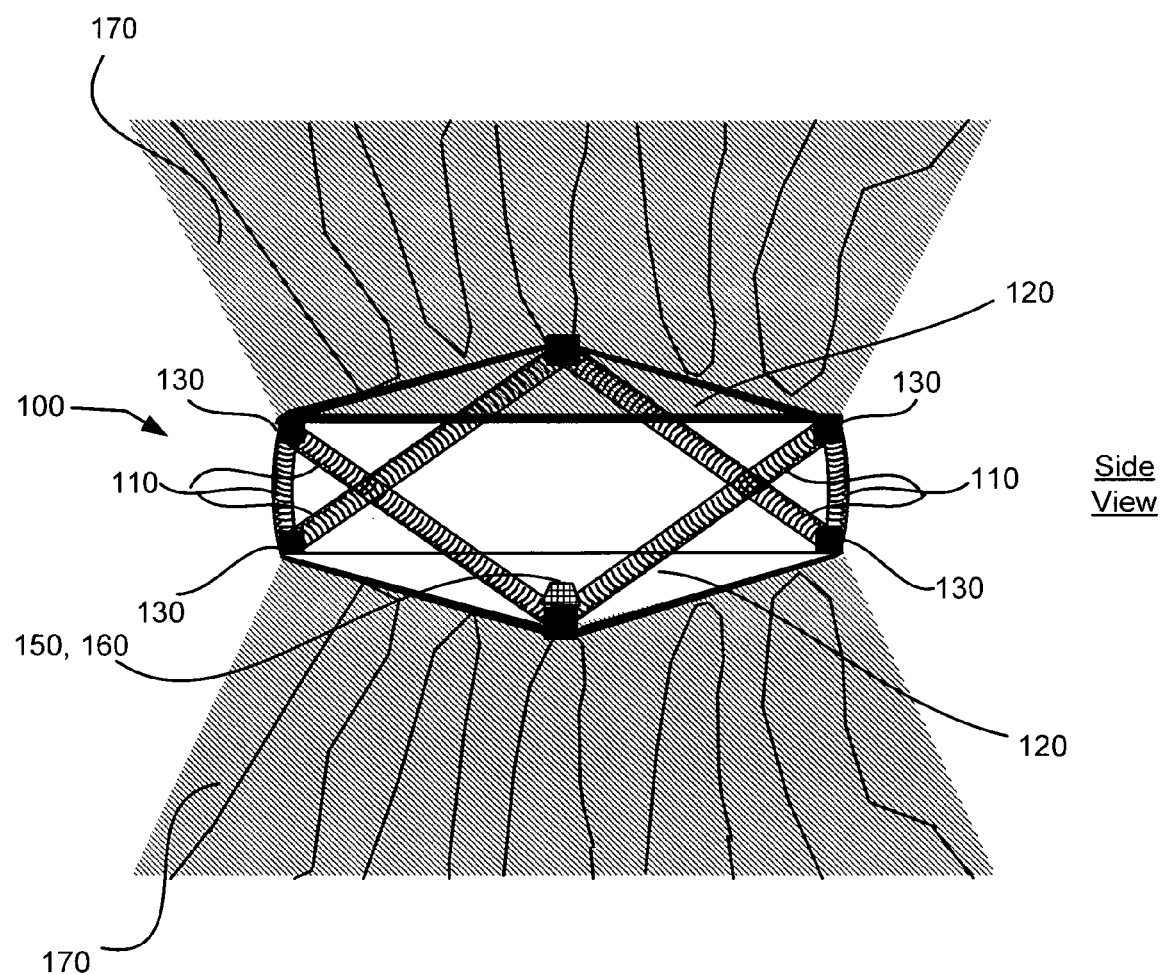

Referring to FIG. 1, depicted is a partial diagrammatic view of an embodiment of an orthopedic implant useful for treating an orthopedic condition in a subject. In FIGS. 1A and 1B, a top view and side view, respectively of an orthopedic implant 100 are shown. The orthopedic implant 100 can include at least one adjustment mechanism 120 configured for securing to at least one orthopedic structure of a subject, and six motors 110A, 110B, 110C, 110D, 110E, 110F operably connected to the at least one adjustment mechanism 120, wherein the at least one motor, including six motors 110A, 110B, 110C, 110D, 110E, 110F, is configured to move the at least one adjustment mechanism in at least three degrees of freedom. In an aspect, the adjustment mechanism 120 is configured to controllably move the internal orthopedic structure in six degrees of freedom. The internal orthopedic structure includes, but is not limited to, bone, cartilage, tendon, or other structural element within the body of the subject. A controller 140 is configured to receive a remote signal to control actuation of the at least one motor 110A-110F and the at least one adjustment mechanism 120. In an aspect, the motors can be remotely-actuated by a controller. The controller 140 is configured to receive the remote signal through a receiver 150. One or more sensors 130A, 130B, 130C, 130D, 130E, 130F are configured to communicate with the controller 140 to report a sensed condition of the orthopedic structure or in response to a sensed change in the orthopedic structure in the subject. A transmitter 160 in communication with the sensor 130A-130F and the controller 140 is configured to report activity of the implant to an external source. Other aspects of the orthopedic implant can include sensors associated with implants or implanted at or near the bones, soft tissue, or joints of the spine and can provide feedback regarding the joint on an ongoing basis. In FIG. 1C, a side view of an orthopedic implant 100 is shown. The orthopedic implant 100 can include at least one adjustment mechanism 120 configured for securing to at least one orthopedic structure 170 of a subject, and six motors 110A, 110B, 110C, 110D, 110E, 110F operably connected to the at least one adjustment mechanism 120, wherein the at least one motor, including six motors 110A, 110B, 110C, 110D, 110E, 110F, is configured to move the at least one adjustment mechanism in at least three degrees of freedom.

Figure 2:
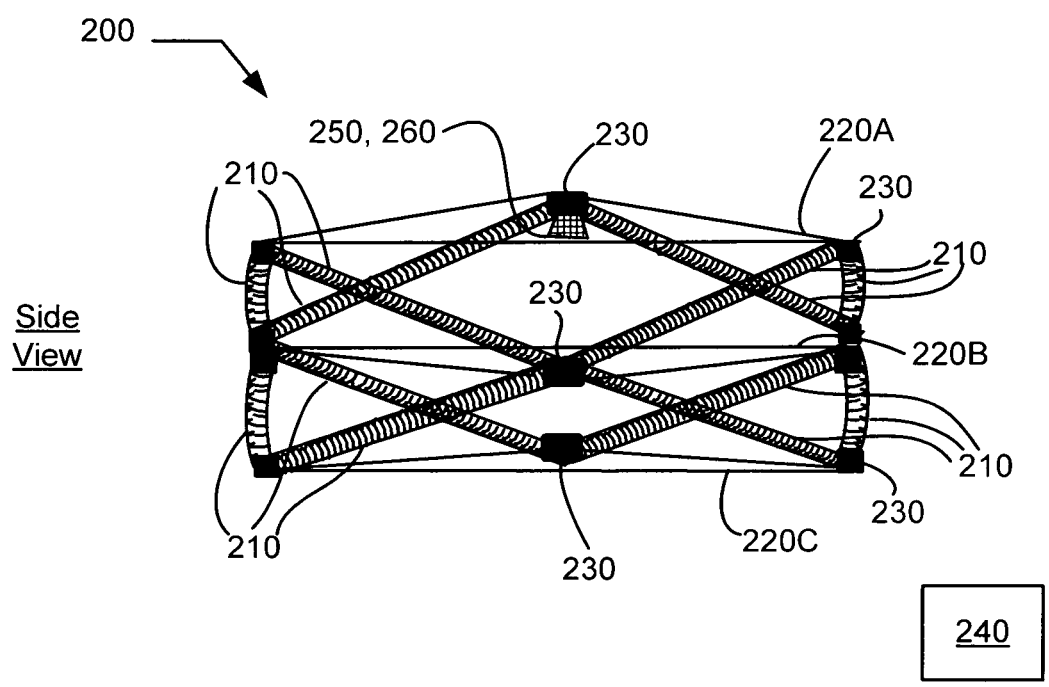
FIG. 2 depicts a diagrammatic view of an aspect of an embodiment of an orthopedic implant.

Referring to FIG. 2, depicted is a partial diagrammatic view of an embodiment of an orthopedic implant useful for treating an orthopedic condition in a subject. In FIG. 2, a side view of an orthopedic implant 200 is shown. The orthopedic implant 200 can include at least one adjustment mechanism 220A, 220B, 220C configured for securing to at least one orthopedic structure of a subject, and six motors 210 operably connected to the at least one adjustment mechanism 220A, 220B, 220C, wherein the at least one motor, including twelve motors 210, is configured to move the at least one adjustment mechanism in at least three degrees of freedom. In an aspect, the three adjustment mechanisms 220A, 220B, 220C are configured to controllably move the subject's orthopedic structure in twelve degrees of freedom. The orthopedic implant 200 includes three adjustment mechanisms 220A, 220B, 220C that provide greater flexibility in at least three degrees of freedom and greater reach of the orthopedic implant to stabilize an internal orthopedic structure within the subject. The subject's orthopedic structure includes, but is not limited to, bone, cartilage, tendon, or other structural element within the body of the subject. A controller 240 is configured to receive a remote signal to control actuation of the motor 210 and the adjustment mechanisms 220A, 220B, 220C. In an aspect, the motors can be remotely-actuated by the controller 240. The controller 240 is configured to receive the remote signal through a receiver 250. One or more sensors 230 are configured to communicate with the controller 240 to report a sensed condition of the orthopedic structure or in response to a sensed change in the orthopedic structure in the subject. A transmitter 260 in communication with the one or more sensors 230 and the controller 240 is configured to report activity of the implant to an external source.

Figure 3:
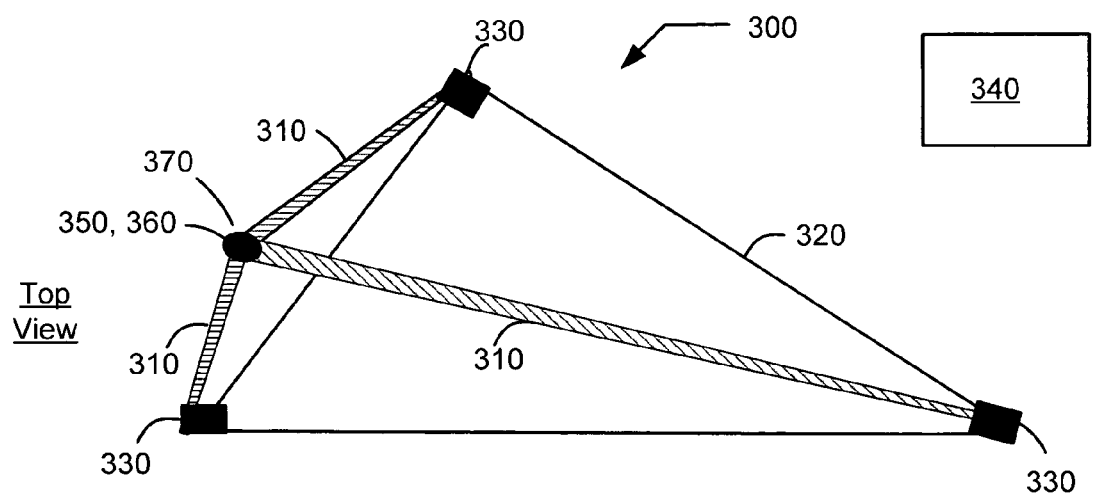
FIG. 3 depicts a diagrammatic view of an aspect of an embodiment of an orthopedic implant.

Referring to FIG. 3, depicted is a partial diagrammatic view of an embodiment of an orthopedic implant useful for treating an orthopedic condition in a subject. In FIG. 3, a top view of an orthopedic implant 300 is shown. The orthopedic implant 300 can include at least one adjustment mechanism 320 configured for securing to at least one orthopedic structure of a subject, and three motors 310 operably connected to the at least one adjustment mechanism 320, wherein the at least one motor, including three motors 310, is configured to move the at least one adjustment mechanism in at least three degrees of freedom. In an aspect, the adjustment mechanism 320 is configured to controllably move the internal orthopedic structure in at least three degrees of freedom. The orthopedic implant 300 includes three motors 310 attached to a location 370 on the orthopedic structure of the subject. This provides the adjustment mechanism 320 greater flexibility in at least three degrees of freedom, for example, in six degrees of freedom. The internal orthopedic structure includes, but is not limited to, bone, cartilage, tendon, or other structural element within the body of the subject. A controller 340 is configured to receive a remote signal to control actuation of the motor 310 and the at least one adjustment mechanisms 320. In an aspect, the motors can be remotely-actuated by a controller 340. The controller 340 is configured to receive the remote signal through a receiver 350. One or more sensors 330 are configured to communicate with the controller 340 to report a sensed condition of the orthopedic structure or in response to a sensed change in the orthopedic structure in the subject. A transmitter 360 in communication with the one or more sensors 330 and the controller 340 is configured to report activity of the implant to an external source. The sensors 330 can be associated with the orthopedic implant or implanted at or near the bones, soft tissue, or joints of the spine and can provide feedback regarding the joint on an ongoing basis.

Figure 4:
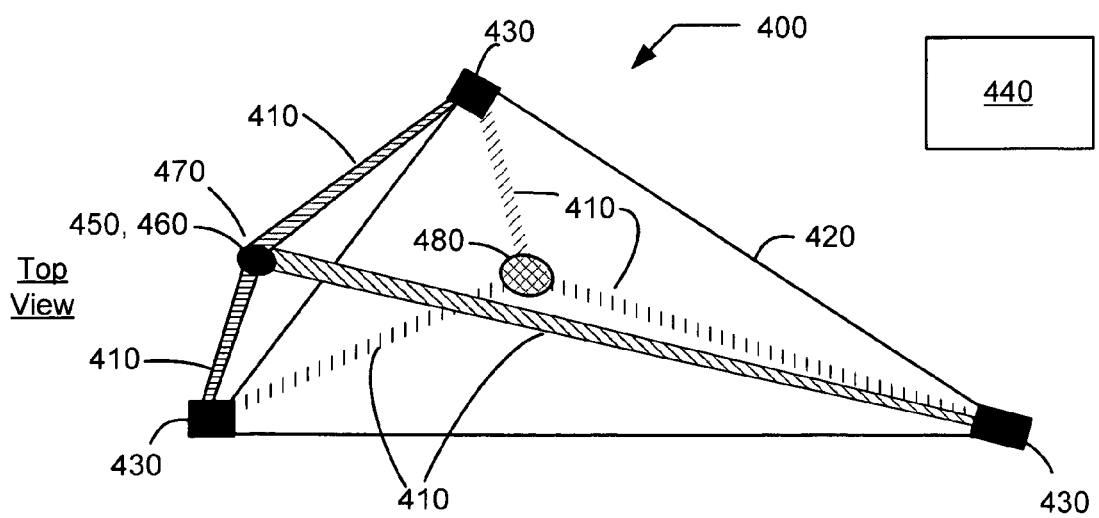
FIG. 4 depicts a diagrammatic view of an aspect of an embodiment of an orthopedic implant.

Referring to FIG. 4, depicted is a partial diagrammatic view of an embodiment of an orthopedic implant useful for treating an orthopedic condition in a subject. In FIG. 4, a top view of an orthopedic implant 400 is shown. The orthopedic implant 400 can include at least one adjustment mechanism 420 configured for securing to at least one orthopedic structure of a subject, and six motors 410 operably connected to the at least one adjustment mechanism 120, wherein the at least one motor, including six motors 410, is configured to move the at least one adjustment mechanism in at least three degrees of freedom. In an aspect, the adjustment mechanism 420 is configured to controllably move the internal orthopedic structure in six degrees of freedom. The orthopedic implant 400 includes six motors 410 wherein three motors 410 are attached to a first location 470 on the orthopedic structure of the subject, and three motors 410 attached to a second location 480 on the orthopedic structure of the subject. This provides the adjustment mechanism 420 with greater flexibility in at least three degrees of freedom, for example, in six degrees of freedom. The subject's orthopedic structure includes, but is not limited to, bone, cartilage, tendon, or other structural element within the body of the subject. A controller 440 is configured to receive a remote signal to control actuation of the motor 410 and the at least one adjustment mechanisms 420. In an aspect, the motors can be remotely-actuated by a controller 440. The controller 440 is configured to receive the remote signal through a receiver 450. One or more sensors 430 are configured to communicate with the controller 440 to report a sensed condition of the orthopedic structure or in response to a sensed change in the orthopedic structure in the subject. A transmitter 460 in communication with the one or more sensors 430 and the controller 440 is configured to report activity of the implant to an external source.

Figure 5:
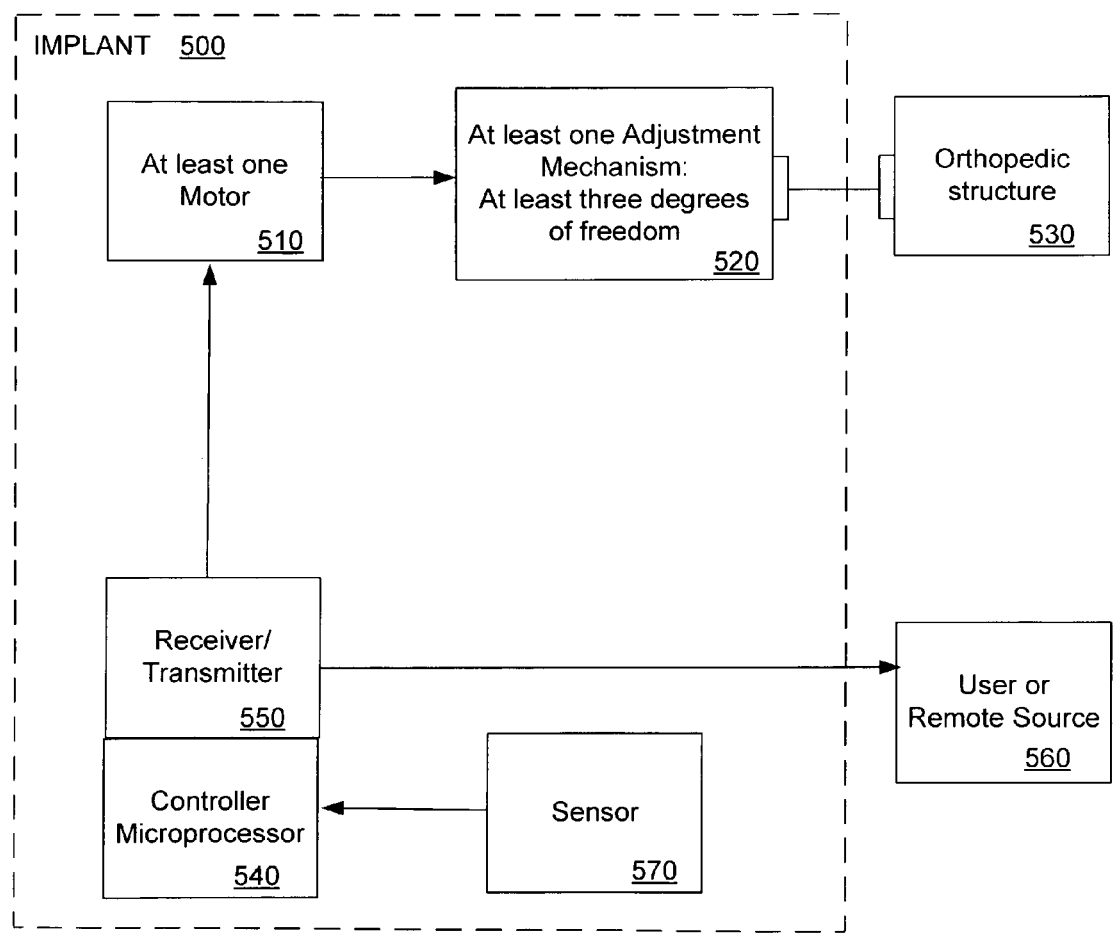
FIG. 5 depicts a diagrammatic view of an aspect of an embodiment of an orthopedic implant.

Referring to FIG. 5, depicted is a partial diagrammatic view of an embodiment of an orthopedic implant 500 useful for treating an orthopedic condition in a subject. In FIG. 5, the orthopedic implant 500 includes at least one adjustment mechanism 520 configured for securing to at least one orthopedic structure 530 of a subject, and at least one motor 510 operably connected to the at least one adjustment mechanism 520. In an aspect, the at least one motor 510 is configured to move the at least one adjustment mechanism 520 in at least three degrees of freedom. A controller 540 can be configured to receive an input signal, and the controller 540 in combination with a receiver/transmitter 550 can actuate the at least one motor. A remote source 560 can be configured to send the input signal. The remote source 560 can further include a human user, data input, or a computer-readable storage medium. Alternatively or in combination with the remote source, a sensor 570 can be configured to send the input signal. The sensor 570 can be configured to inform the controller 540 in response to a sensed condition of the orthopedic structure. A receiver/transmitter 550 can be in communication with the sensor 570 and the controller 540, wherein the receiver/transmitter 550 can be configured to report activity of the implant to an external source 560.

Figure 6:
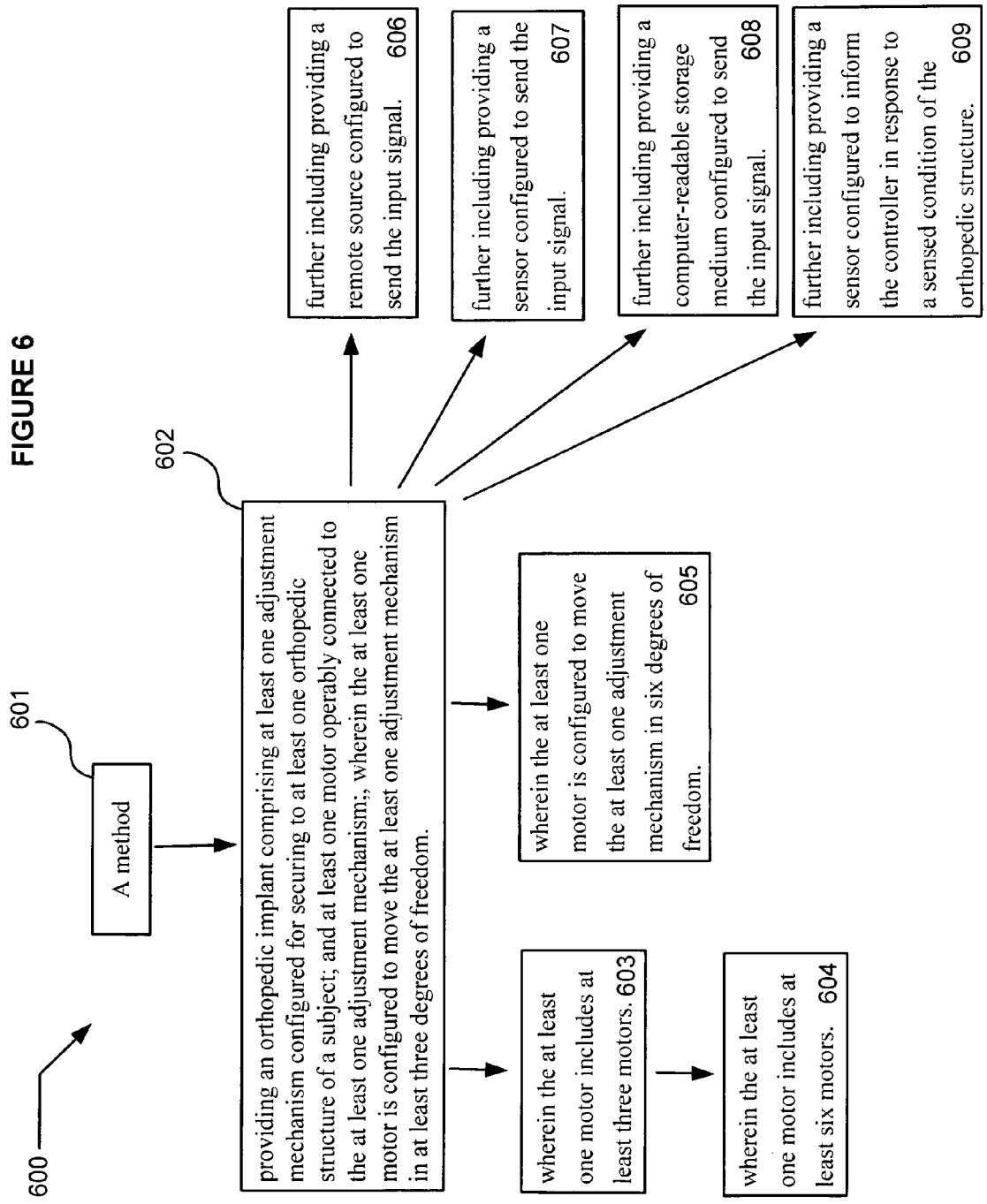
FIG. 6 depicts a logic flowchart of a method for treating an orthopedic condition in a subject.

Referring to FIG. 6, a logic flowchart is depicted for a method for treating an orthopedic condition in a subject. The method 601 includes providing 602 an orthopedic implant comprising at least one adjustment mechanism configured for securing to at least one orthopedic structure of a subject; and at least one motor operably connected to the at least one adjustment mechanism;, wherein the at least one motor is configured to move the at least one adjustment mechanism in at least three degrees of freedom. The at least one motor can include at least three motors 603 or can include at least six motors 604. The at least one motor can be configured to move the at least one adjustment mechanism in six degrees of freedom 605. The method can further include providing a remote source configured to send the input signal 606. The method can further include providing a sensor configured to send the input signal 607. The method can further include providing a computer-readable storage medium configured to send the input signal 608. The method can further include providing a sensor configured to inform the controller in response to a sensed condition of the orthopedic structure 609.

An orthopedic implant can provide distraction forces to, for example, relieve pressure on certain structures, compression forces to fix or stabilize motion across structures, shock absorbing qualities to help relieve load from certain structures, and therapeutic activity to reduce inflammation and pain. The orthopedic implant can include at least one adjustment mechanism configured for securing to at least one orthopedic structure of a subject, and at least one motor operably connected to the at least one adjustment mechanism, wherein the at least one motor is configured to move the at least one adjustment mechanism in at least three degrees of freedom, and up to six degrees of freedom, to vary a configuration of an internal orthopedic structure in the subject. Other aspects of the orthopedic implant as described herein can supplement or bear load for degenerated, painful, or surgically removed joints, e.g., the facet joint. Another aspect of the orthopedic implant can provide a method and system for treating an orthopedic condition, including deformities such as scoliosis. In a further aspect, the orthopedic implant can include sensors associated with implants or implanted at or near the bones, soft tissue, or joints of the spine and can provide feedback regarding the joint on an ongoing basis. The sensors can also be part a feedback system to a controller and transmitter that alters a property of an implant in response to sensing information.

In an aspect, an orthopedic implant and method for treating an orthopedic condition in a subject includes alleviating discomfort and or deformity associated with a condition of the spinal column. An aspect of the orthopedic implant includes at least one adjustment mechanism configured for securing to at least one orthopedic structure of a subject, and at least one motor operably connected to the at least one adjustment mechanism, wherein the at least one motor is configured to move the at least one adjustment mechanism in at least three degrees of freedom, to vary a configuration of an internal orthopedic structure in the subject. The method for treatment as described herein is directed to providing a minimally invasive orthopedic implant useful in a method for alleviating discomfort associated with the spinal column. Another aspect provides a minimally invasive, non-invasive, or remote adjustment or lengthening of an orthopedic implant. A further aspect provides a minimally invasive, non-invasive, or remote adjustment or lengthening of an orthopedic implant that is a stabilization or distraction device. A further aspect also provides an orthopedic implant suitable for minimally invasive, minimally disruptive and/or percutaneous posterior deployment across a plurality of motion segments and more than two motion segments in a diseased or shattered bone, or diseased spine. Different aspects can provide distraction forces to relieve pressure on certain structures, compression forces to fix or stabilize motion across structures, shock absorbing qualities to help relieve load from certain structures, and therapeutic activity to reduce inflammation and pain.

The present disclosure can be utilized in the construction of a femoral orthopedic implant for implantation using minimally invasive techniques. These and other hip orthopedic implant can be used in either primary or revision procedures. The present disclosure can also be used in the construction of an adjustable tibial tray for use in a knee procedure. The present disclosure can also be used in the construction of a spinal implant used to treat, amongst other things, scoliosis. The present disclosure can also be used in the construction of fracture management devices thereby providing the device with the ability to compress a fracture site through external fixators, nails, and/or plates. The present disclosure can also be used in the construction of expandable and contractible nails for use in, e.g., trauma procedures.

In an aspect, the orthopedic implant can be utilized as a spinal stabilization device. Certain spine conditions, defects, deformities (e.g., scoliosis) as well as injuries may lead to structural instabilities, nerve or spinal cord damage, pain or other manifestations. Back pain (e.g., pain associated with the spinal column or mechanical back pain) may be caused by structural defects, by injuries or over the course of time from the aging process. For example, back pain is frequently caused by repetitive and/or high stress loads on or increased motion around certain boney or soft tissue structures. The natural course of aging leads to degeneration of the disc, loss of disc height, and instability of the spine among other structural manifestations at or around the spine. With disc degeneration, the posterior elements of the spine bear increased loads with disc height loss, and subsequently attempt to compensate with the formation of osteophytes and thickening of various stabilizing spinal ligaments. The facet joints may develop pain due to arthritic changes caused by increased loads. Furthermore, osteophytes in the neural foramina and thickening of spinal ligaments can lead to spinal stenosis, or impingement of nerve roots in the spinal canal or neural foramina. Scoliosis also creates disproportionate loading on various elements of the spine and may require correction, stabilization or fusion utilizing an orthopedic implant as described herein. The orthopedic implant, including at least one motor configured to move at least one adjustment mechanism in at least three degrees of freedom can act as a support structure for vertebrae of the spine positioned over a posterior portion of a spinous process with wings over the lamina including small screws into lamina. The adjustment mechanism can be attached to pedicle screws anchored into pedicles and further anchored into the spinous process through screws positioned through holes in the adjustment mechanism. The adjustment mechanism can include a sensor that can be used to sense loads on the device. The adjustment mechanism is configured to controllably move in at least three degrees of freedom, including up to six degrees of freedom, or including up to twelve degrees of freedom, to vary a configuration of the vertebrae in the spine of the subject. The pedicle screw includes a screw capture device for receiving a screw or rod of a spinous process screw or other rod. The adjustment mechanism can be a polyaxial head of a pedicle screw. The adjustment mechanism can include a hole, or a threaded screw hole with a washer or cap. A cross bar can be positioned across the spine between heads of pedicle screws to prevent pedical screws from creeping laterally. A wedge shaped nut between the head of the screw and the adjustment mechanism. Another nut can be positioned between adjustment mechanism and pedicle screw, and secure against the adjustment mechanism of the orthopedic implant. See, e.g., U.S. Application No. 2006/0036259.

In an aspect, the orthopedic implant as described herein can be remotely lengthened after surgery, as needed. For example, the gait of patients after hip replacement surgery may be affected if the leg length of one limb is longer or shorter than the other. The orthopedic implant allows doctors to change the implant's length over time as needed to help restore normal gait. Other indications include surgical procedures where an external fixator is used in long bone fractures. In an aspect, a distractor can be affixed at opposite ends, to opposite sides of other structures of the body, including, for example a hip joint. The orthopedic implant including the distractor as part of the adjustment mechanism configured to controllably move in at least three degrees of freedom, or in six degrees of freedom including up to twelve degrees of freedom, to vary a configuration of an orthopedic structure of the hip in a subject. The distractor can be remotely moved or less invasively accessed for distraction adjustments, including, e.g., post operatively, over the life of the prosthetic implant, or over time.

The orthopedic implant provides distraction systems that are contemplated for distracting the adjacent vertebrae in at least three degrees of freedom, e.g., an expandable screw or rod or plate, telescoping implant, a distraction jack, an inflatable column, a column that lengthens when exposed to heat, fluids, ultrasound, or other biological, physical, or chemical catalysts, e.g., using a device constructed of a shape memory alloy or rheostatic fluids. The amount of distraction may be controlled remotely, by radiofrequency, electromagnetic energy, electrical, heat, ultrasound, and other means. In an aspect, the orthopedic implant can include at least one adjustment mechanism that is a distracting member comprising a remotely moved realignment device or solenoid. The distraction can also be adjusted percutaneously or remotely according to one of these variations. The adjustments can be made over time, particularly if the disease progresses or other anatomical changes occur. This would allow the orthopedic implant to adjust the amount of distraction as needed to a patient's symptoms long after surgery. The distraction adjustment can also be done with patient feedback. The orthopedic implant including at least one motor configured to move a distraction adjustment mechanism can also include a variety of different types of sensors that sense changing loads on the spine or on the device. For example, the orthopedic implant can be a distraction device including a pressure sensor or a strain gauge. The sensor can be configured to detect one or more of strain, pressure, motion, stress, load, or position change of the orthopedic structure. The orthopedic implant including at least one motor configured to move a distraction mechanism with spring properties can include a freeze or lock that permits the device to be immobilized should a fusion type procedure be necessary to immobilize a patient's spine, for example, at a later date with further wear or progression of disease. The orthopedic implant including at least one motor configured to move a distraction mechanism can also include a locking mechanism, e.g., a ratchet, to lock the relative position of the adjustment mechanism, e.g., a stem assembly and a body assembly of the distraction device. The flexibility or stiffness of the orthopedic implant can also be incrementally or progressively adjusted. The orthopedic implant including at least one motor configured to move a distraction mechanism can also include a fuse-like feature or a predetermined failure feature so that the implant breaks first before a bone fractures from stresses related to the device implant. This may be accomplished by determining the approximate failure properties of the bones at the location of implant and by designing the distraction rod to fail at a force below the force required to fracture the bone.

In an aspect, the orthopedic implant can include at least one motor configured to move at least one adjustment mechanism that includes a spinous process screw that can be configured to exert flexible, stabilizing, nonfusion forces through the adjustment mechanism in at least three degrees of freedom, e.g., in six degrees of freedom, to vary a configuration of a spinal structure in a subject. The orthopedic implant can be used in the event that patient suffers from pain due to laxity of the spinal structures, e.g., degenerative spondylolisthesis, wherein the looseness of the joint may cause pain. In an aspect, an orthopedic implant and method is described for dynamically stabilizing or reducing such a joint while allowing some flexibility and movement. The orthopedic implant can provide such stabilization on an oblique angle with respect to the rotational axis of the spine, i.e., at an oblique angle with respect to the median and horizontal planes of the spine. The spinous process and a pedicle are used to anchor a device exerting a stabilizing or compression or contractile force between the two anchors on an oblique angle, and allowing controlled movement in at least three degrees of freedom. The orthopedic implant can be used to exert a contractile force and can be constructed from materials including, but not limited to, polymeric materials, super elastic metals, and fabrics. The spinous process screw includes a sensor that can be used to sense motion of the orthopedic implant. The forces or stresses on the device can be monitored and used to determine whether it may be necessary to convert the device to a fusion type device, or to otherwise reduce motion. The sensor can also be used as a diagnostic device to measure the amount of joint motion upon insertion of the implant or over time. The orthopedic implants described herein can include a sensor that can be used to sense one or more parameters, e.g., strain, pressure, motion, stress, load, or position or change. The sensor can provide information about possible screw failure. The sensor can communicate the information to an external device, e.g. telemetrically, and can be passively powered by an external device.

In an aspect, the orthopedic implant can be a femoral implant that includes at least one motor configured to move at least one adjustment mechanism to controllably move the implant in at least three degrees of freedom, e.g., in six degrees of freedom, or up to twelve degrees of freedom. The femoral implant is adjustable post-operatively to correct a surgical error or otherwise account for surgical variation such as leg length discrepancy subsequent to a hip replacement procedure; or for post-operative correction of instability issues arising from compromise of the patient's soft tissue, e.g., tissue stretching. The orthopedic femoral implant as described herein can be used to increase stability of a total hip replacement. The orthopedic femoral implant can be used to improve weak abductor function in a total hip replacement. The orthopedic implant is configured to be implanted into the femur of a patient in order to replace certain natural features of the patient's femur as a result of, for example, disease or trauma. The orthopedic implant can be implanted into a surgically prepared, e.g., reamed and/or broached, medullary canal of the femur. See, e.g., U.S. Application No. 2006/0069447.

In an aspect of the femoral orthopedic implant, the at least one adjustment mechanism can include, but is not limited to, a stem assembly, a body assembly, and a neck of the orthopedic implant. Each of the stem assembly, the body assembly, and the neck of the orthopedic implant can be made of materials conventionally utilized in the construction of prosthetic implants. For example, the stem assembly, the body assembly, and the neck can be constructed from implantable metals such as stainless steel, cobalt chrome, or titanium, including alloys of such metals. The stem assembly, the body assembly, and the neck can also be constructed with non-metallic materials such as implant-grade polymers or ceramics. The stem assembly can be embodied in a number of different configurations in order to fit the needs of a subject's anatomy and provide a variety of geometries and sizes, e.g., relatively long stem assembly for use with a long femur, a relatively short stem assembly for use with a short femur. The stem assembly can also be embodied in a bow-shaped configuration if required by a given patient's anatomy. In a further aspect, the stem assembly can also be embodied in various diameters as required by a given patient's anatomy. The orthopedic implant as described herein can be utilized in the construction of a prosthesis for implantation into the humerus, radius, ulna, tibia, fibula, femur, glenoid, talus, spine, or any of the metatarsals or metacarpals.

In an aspect, the orthopedic implant can be a tibial implant that includes at least one adjustment mechanism to controllably move the implant in at least three degrees of freedom, e.g., up to six degrees of freedom. Post-operative adjustment to correct any tibial tray malalignment that may occur following a total knee replacement procedure; post-operatively correct the occurrence of subsidence on either one side (medial), or both sides (medial and lateral) of the knee; anterior/posterior adjustment of the implant; correction of instability issues arising from surgical error or compromise of soft tissue; raising the proximal surface of the tibial tray. See, e.g., U.S. Application No. 2006/0069447.

Remote actuation of the orthopedic implant can be achieved through use of, e.g., a wireless communications link to the at least one motor configured to move at least one adjustment mechanism. For example, a radio-frequency (RF) or acoustic link can be used to communicate commands to the implant and the at least one motor once the implant has been placed in the subject.

The orthopedic implant can be configured to include any necessary hardware and software to perform the desired functions. For example, the implant can be configured with a number of motors, sensors, transmitters, receivers, and other mechanisms to perform and measure an action and provide feedback to the user (e.g., the surgeon or physician).

Hardware and software to perform desired functions includes one or more of the following:

Power source can be used to power motors, sensors, and electronics;

Energy to actuate the motors, or other devices, can also be externally provided to the implant (e.g., transcutaneously);

As illustrated in FIGS. 1 through 5, a sensor can be positioned on the orthopedic implant or on the orthopedic structure of the subject. Multiple sensors may be placed on each of the implant and the orthopedic structure. The sensor can be embedded in material in the orthopedic implant. The sensor can sense stress on the orthopedic structure from implants secured to it, or can sense other information that may be desirable to monitor. In an aspect, the sensor can be configured to detect health or integrity of the orthopedic structure; the sensor can be configured to detect ultrasound through the orthopedic structure or conductivity of the orthopedic structure; or the sensor is configured to detect an osteogenic cell marker. The sensor can include a controller or communication element configured to communicate sensed information to an external device, e.g., when interrogated. The controller can be configured to receive an input signal to control actuation of at least one of the at least one motors. The input signal can be from a remote source, from a sensor, or from a computer-readable storage medium. The orthopedic implant can further include a transmitter in communication with the sensor and the controller, the transmitter configured to report activity of the implant to an external source, wherein the external source includes, but is not limited to, a human being or computing device. The transmitter can be further configured to report activity of the implant including the sensed condition of the orthopedic structure. The transmitter can be in communication with the sensor and the controller, wherein the transmitter is configured to send an actuation signal to the at least one motor.

A sensor feedback mechanism can facilitate external actuation of the orthopedic implant. The implant can be actuated by a transcutaneous source or controller, with the control of such a source utilizing input from a sensor associated with the orthopedic implant. The sensor can be used to identify the need for actuation of the at least one motor by the controller. During such actuation, the sensor provides feedback to monitor the movement or the orthopedic implant.

An adjustable remote-controllable orthopedic implant can be designed that is adjustable and remotely controlled, such that the implant can be actuated via transcutaneous energy transfer and/or an onboard power source so that the shape, size, offset, alignment, or length of the orthopedic implant can be adjusted. Multiple motors can be utilized. A sensor, or multiple sensors, can be used to provide real-time feedback to the surgeon. Such feedback may be provided to the surgeon via any type of human machine interface. This feedback may be used to facilitate adjustment of the implant to a desired orientation/position.

The orthopedic implant can include a sensor that includes a joint space narrowing measurement device. The sensor including the joint space narrowing measurement device can be used to monitor the distance between two bones, including any implants placed in them, and provide adjustments to the orthopedic implant to actuate the at least one motor to move the at least one adjustment mechanism in at least three degrees of freedom, e.g., in six degrees of freedom or up to twelve degrees of freedom, to vary a distance between two bones, including implants, in a subject. The device can also be used to monitor the relative three-dimensional position and orientation of an implant component, e.g., the tibial component of a knee prosthesis, with respect to another implant component, e.g., the femoral component of a knee prosthesis, and provide controllable adjustments in at least three degrees of freedom. As the joint space narrows, the device enables a surgeon to identify the narrowing profile, e.g., medial or lateral dominant or a precise relative position and orientation of one component with respect to another indicating levels of subsidence, migration, fixation integrity, and potentially micromotion. A controller can include an actuator of the at least one motor. The actuator can include, but is not limited to, magnet-driven actuator; transcutaneously energized actuator; or on board power source. Real time feedback of the position of the adjustment mechanism improves the adjustment and increases likelihood of the proper adjustment.

The internal or on-board power source of the orthopedic implant can be embodied in numerous forms. Motors can include, but are not limited to, one or more stepper motors, drive motors, servomotors, piezoelectric actuators, ultrasonic power with an ultrasonic actuator to drive a piezoelectric motor (SQUIGGLE® ultrasonic actuator motor, New Scale Technologies, Inc., Victor, N.Y.), shape memory alloy actuators, paraffin actuators, linear piezoelectric motors, electromagnetic solenoids, electroactive polymers, to drive the movable components of the implant. Such devices can be driven by a spring bias, fluid pressure, gas pressure, electric current, heat (e.g., nitinol or other shape memory alloy changing shape as a function of temperature change), or other types of energy. For example, the power source can be an on-board battery, such as a lithium iodine cell available from Wilson Greatbatch Technologies, Inc. (Clarence, N.Y.). Alternatively, the power source can be internal or external and derived from an ultrasonic power source.

In an aspect, the internal power source of the orthopedic implant can be an inductive power source such as a ferrite-loaded coil. A suitable ferrite-loaded coil is a small wound coil such as that available commercially from Predan SA (Campanillas, Malaga, Spain). The configuration of such a wound coil can be based on the design and the selection of the electronic components of the orthopedic implant. For example, the power, frequency, and size of the coil can be selected to suit the other components of the orthopedic implant. Alternatively, a suitable ferrite-loaded coil can be wound using standard equipment such as that available from Aumann North America, Inc. (Fort Wayne, Ind.). When the coil is passed through an externally generated electromagnetic field, an electric current is formed through the coil that can be used to power the other components within the orthopedic implant. Other suitable power sources or power generators can be used as well.

In an aspect, the power source includes an inductor, an external power source can be provided at the point of care. The external power source can form a component of an external control system, and can include a coil that generates a localized electromagnetic field that acts upon the implanted ferrite coil to thereby supply power to the implanted electronics. Suitable external coils are commercially available from Predan SA (Campanillas, Malaga, Spain). Generally, since the coils are likely to be used in close proximity to the patient, it may be desirable to select or design a coil that will not irritate or excessively heat the subject's skin and that can be easily handled by the operator or medical technician. The coil supplies a field at the desired frequency to stimulate the implanted power coil. The external control system can also include a remote receiver or transceiver to receive an output signal from any sensor that can be positioned on or within the orthopedic implant. An internal transmitter or transceiver associated with the controller of the orthopedic implant can then operate to transmit the sensor's signal to the external control system. The external control system can include other components as well. The internal transmitter/transceiver can respond to the controller by transmitting a signal to actuate the at least one motor.

The at least one motor that is configured to move the at least one adjustment mechanism can include, but is not limited to, an electronic motor, electrostrictive motor, piezoelectric motor, ultrasonically-activated motor, shape memory alloy actuator, paraffin actuator, electromagnetic solenoid, or electroactive polymer. The motor can be a DC stepper motor, a DC motor, drive motor, servomotor, or a rotary piezoelectric motor that has a rotational output. Suitable motors sized to fit within an orthopedic implant, include, for example, those sold by MicroMo Electronics, Inc (Clearwater, Fla.), Sanyo (Bensenville, Ill.), and/or Aeroflex, Motion Control Products Division (Hauppauge, N.Y.). The gear reducer includes an input shaft coupled to the output shaft of the motor, a system of gears, and an output shaft coupled to the threaded drive shaft to rotate the threaded shaft in both an advancing direction and a retracting direction. The gears within the gear reducer operate to reduce the rotational speed of the output shaft of the gear reducer as compared to that of the output shaft of the motor.

Ultrasonic power can be used with an ultrasonic actuator to drive a piezoelectric motor (SQUIGGLE® ultrasonic actuator motor, New Scale Technologies, Inc., Victor, N.Y.). Ultrasonic motors comprising a threaded nut (e.g., lead zirconate titanate, PZT; lead metaniobate, PN; lead nickel niobate, PNN) and screw utilize two phase drive signals causing piezoelectric actuators to vibrate the nut at a fixed resonant frequency, e.g., a two-channel sinusoidal or square wave at an ultrasonic frequency of 40 kHz to 200 kHz, matching the first bending resonant frequency of the threaded tube. This creates an orbital motion that drives the screw in a bidirectional translational direction.

The drive assembly can include a motor, e.g., an ultrasonically actuated piezoelectric motor, having a linearly moving output shaft coupled to the body assembly to linearly translate the body assembly relative to the stem assembly. The piezoelectric motor is electrically coupled to the power source. Similarly, multiple drive assemblies each including a piezoelectric motor can be electrically coupled to the power source and have a linearly moving output shaft coupled to the other components of the orthopedic implant to linearly translate the components relative to the body assembly. Each of the piezoelectric motors can include a piezoelectric actuator, for example, one sold by New Scale Technologies, Inc., Victor, N.Y.), APC International, Ltd. (Mackeyville, Pa.) and/or by Piezosystem Jena, Inc. (Hopedale, Mass.), a shape memory alloy actuator, for example, one sold by NanoMuscle, Inc. (Antioch, Calif.), a paraffin actuator, for example, one sold by Stansys Research Corporation (Boulder, Colo.), a linear servomotor, for example, one sold by Anorad Rockwell Automation (Shirley, N.Y.) and/or Nippon Pulse America, Inc. (Radford, Va.), a linear piezomotor, for example, one sold by Nanomotion, Inc. (Ronkonkoma, N.Y.), an electromagnetic solenoid, or a non-commutated DC linear motor such as, for example, one sold by H2W Technologies, Inc. (Valencia, Calif.). Other suitable linear motors can be used as well. For example, a suitable linear piezomotor can include a linear piezomotor capable of producing enough force to move the at least one adjustment mechanism, e.g., a body assembly relative to a stem assembly and to move a neck relative to a body assembly. Further, any suitable linear piezomotor includes those linear piezomotors sized to fit within a standard orthopedic implant, such as orthopedic implant, and/or any other type of orthopedic implant where movement of two portions relative to one another is desired. Additionally, other linear piezomotors can include linear piezomotors that provide actuator forces via bending or flexing movements such as, for example, an electroactive polymer (EAP) actuator.

A physician, nurse, physical therapist or other user may adjust the length and/or offset of the orthopedic implant through remote control using a wireless communications link. For example, the external control system can include a user interface, such as a laptop or PC, hand-held personal computer, personal data assistant, or any custom-designed data acquisition device, for example, having a wireless link for communication with the controller of the orthopedic implant. The controller can be embodied as any type of electronic controller such as, for example, general purpose microcontrollers, microprocessors, or application specific integrated circuits (ASICs). Moreover, the controller can further include a receiver, transmitter, or transceiver and a memory device such as a random access memory (RAM) device. The controller is configured with the appropriate hardware, software, and/or firmware to be responsive to the user commands received via the external control system.

The controller of the orthopedic implant is configured to include a receiver mechanism for receiving an input signal and a transmitter for sending a signal to at least one motor or to an outside source. See, for example, FIG. 5. The controller can include a microprocessor or other processor to convert the received input signal into an appropriate output signal. The controller can include a transmitter mechanism that transmits a control signal to control actuation of the at least one motor. The controller is configured to communicate with the sensor and with the external control system by use of at lest one transmitter (transceiver). The communication link between the sensor, the controller, and the external control system can use any type of suitable communication technology, such as radio frequency (RF) or an acoustic link. In an aspect, the controller transmits data received from the sensor to the external control system. In an alternative aspect, the controller transmits data received from the sensor to the internal control system. In the case of a position sensor, the controller transmits data indicative of the relative position of one or more of the components of the orthopedic implant (e.g., the adjustment mechanism). The external or internal control system can then display such data to the surgeon via a display device, such as a monitor, associated with the system's user interface. Armed with this information, the surgeon may then adjust the orthopedic implant. For example, the external or internal control system can communicate with the controller to, for example, adjust the length and/or the offset of the adjustment mechanism of the orthopedic implant. For instance, the external or internal control system can transmit signals to the controller that cause the controller and transmitter to actuate the motors of the respective drive assemblies of the orthopedic implant.

A physician, nurse, physical therapist or other user can communicate with the controller to instruct the at least one motor of the respective adjustment mechanism to rotate in a first or second direction a particular number of rotations or for a particular length of time in order to control the adjustment of the orthopedic implant in at least three degrees of freedom. For example, a physician, nurse, physical therapist or other user may send a wireless signal to instruct either motor to rotate five revolutions in a particular direction. Alternatively, a physician, nurse, physical therapist or other user may simply enter a particular distance or select from a menu a particular distance, e.g., 5 mm, as an amount by which the user would like one or more of the components of the orthopedic implant to be adjusted.

The orthopedic implant can include a variety of onboard sensors gathering data and relaying that data back to the user interface of the external control system. For example, the orthopedic implant can include one or more position sensors. The controller of the orthopedic implant can also include a modulator to convert the output position signals of the position sensor to an encoded signal that can be transmitted from the transmitter within the controller to a location outside the patient's body (e.g., the external control system). The sensor can be made from a polymer material to allow RF or other signals to be transmitted therethrough.

The modulator can encode a particular position output signal into an RF wave by means of varying signal amplitude, frequency, or phase. The output from the modulator is transmitted outside of the patient's body by use of the transceiver's antenna. The external control system demodulates and displays the data for the surgeon or other technician to read on the user interface. The surgeon or other technician is provided with real-time feedback as to the position of the components of the orthopedic implant.

In an aspect, the controller of the orthopedic implant allows signals to be transmitted from and received by the transmitter and receiver within the orthopedic implant. In an aspect, a modulator can be positioned within the adjustment mechanism or the motor and is electrically coupled to the power source. Suitable modulators are commercially available from Texas Instruments, Inc. (Dallas, Tex.) in the form of electronic chips. The modulator and transmitter can be provided as separate elements or can be provided as a single element capable of performing both these functions. The transmitter/receiver can include a modulator or a modulating component. The modulator is also electrically coupled to and powered by the power source.

The transmitter/receiver of the controller can include an antenna, such as a radiofrequency (RF) antenna in the case of when RF technology is used, to receive signals from the antenna of the orthopedic implant. The external control system can be programmed to demodulate the RF signal transmitted from the antenna of the orthopedic implant. The external control system can be programmed to perform calculations necessary to convert the received and demodulated signal to the position sensed by the position sensor. The external control system can also be used to send instructions to the controller of the orthopedic implant to allow a surgeon or other technician to remotely operate the orthopedic implant. The transmitter/transceiver of the external control system can be operated to generate signals (e.g., RF signals) that are received by the antenna of the orthopedic implant.

Such signals can include commands regarding the control of one or more of the motors of each of the respective drive assemblies of the orthopedic implant wherein the adjustment mechanism is configured to controllably move in at least three degrees of freedom to vary a configuration of an internal orthopedic structure in a subject. The controller of the orthopedic implant can include a demodulator capable of demodulating and reading the signal as a set of instructions for operating the one or more motor of the one or more drive assemblies. For example, a user may type a set of instructions into the user interface device of the external control system, thereby operating the one or more remotely-actuated motors of the drive assembly to rotate a predetermined number of rotations (e.g., five rotations). This instruction signal is then sent from the external control system to the orthopedic implant to cause the remotely-actuated motor to rotate as instructed to then cause the body assembly to translate a certain distance, e.g., 5 mm.

To increase the length of the orthopedic implant, such as may be needed from time to time when a femoral orthopedic implant is implanted in a growing child, a wireless transmission of instructions can be sent to the orthopedic implant from a point of care computer to adjust the length and/or offset of the orthopedic implant. The internal power source powers the motors of the one or more drive assemblies that in turn rotate the respective threaded drive shaft to cause either axial movement of the adjustment mechanism, e.g., a body assembly, along one or more axes or to cause axial movement of the adjustment mechanism, e.g., neck assembly, along the one or more axes. Such extension of the body assembly increases the length of the orthopedic implant, while extension of the neck increases the both the offset and the length of the orthopedic implant. It should also be appreciated that the external control system activates the respective motors to effectuate rotation of the threaded drive shafts transcutaneously thereby eliminating the need to surgically gain access to the orthopedic implant to increase the length and/or offset thereof. Similarly, to decrease the length and/or offset of the orthopedic implant, such a command can be transmitted via an RF signal to the orthopedic implant as well.

In an aspect, one or more displacement sensors can be incorporated into the orthopedic implant. For example, the orthopedic implant can be embodied with sensors including, but not limited to, one or more Hall effect sensors, linear variable displacement transducers (LVDT's), differential variable reluctance transducers (DVRT's), or reed switches. Such sensors can be incorporated into the femoral stem and neck of the remotely-adjustable orthopedic implant and used to measure the distance extended between two components. For example, the sensors can be used to monitor the change in length of the stem and/or the neck in real-time while the orthopedic implant is being adjusted. In a detailed aspect, a Hall effect sensor can be used to monitor the position of the femoral stem and/or neck. During adjustment, the sensor can be used to provide real-time feedback. In addition to the orthopedic implant, such sensors and schemes can also be utilized in the construction of other types of orthopedic implants.

In a further aspect, the output from a position sensor can be used by the controller to adjust the orthopedic implant in response to a change in the position of the femoral component with respect to the femur in which it is implanted. For example, as the femoral component subsides and therefore changes its position with respect to the femur, the stem can be extended to compensate for the subsidence. The sensor, that can exemplarily be located on the adjustment mechanism, e.g., on the moving shaft, continues to monitor its position with respect to the femur. When the sensor has reached a position with respect to the femur that is within predetermined limits, adjustment of the orthopedic implant ceases. In addition to the orthopedic implant, such sensors and schemes can be utilized in the construction of other types of orthopedic implants.

An orthopedic implant including at least one motor configured to move at least one adjustment mechanism is described that includes a reinforcement structure for supporting the spinous process and if desired, in addition, the lamina of a spine, e.g., for securing portions of the orthopedic implant to the spine. An orthopedic implant and a method and system for forming or implanting such structure in the spinous process or a region of cancellous bone in the lamina of a spine is described. The reinforcement system can include one or more systems of reinforcement and can be used before, during and/or after a spinal device, e.g., a stabilization, distraction or prosthetic device, is coupled to the spinous process.

The orthopedic implant described herein can be coupled to the spinous process using minimally invasive techniques. These techniques can include percutaneously accessing the spinous process and/or using dilators to access the spinous process at an oblique angle with respect to median plane m and/or horizontal plane h through the spine of the patient. An oblique skin stab wound is made to navigate to the spinous process, that can be exposed under direct vision. The spinous process screw or other distraction device is then screwed or positioned through the spinous process across or through the facet joint, and into a pedicle screw or attachment device stabilizing the facet joint. A similar screw can also be placed from the spinous process to the contralateral pedicle. The spinous process can be reinforced prior to or after placing the screw or other distraction device. See, e.g., U.S. Application No. 2006/0036259.

An aspect provides a distraction device that distracts the joint in an upward or in less of a forward bending manner diminishing kyphosis formation. The orthopedic implant, e.g., distraction device, as described herein lessens spinal stenosis and reduces stress on the facet joints. In an aspect, narrowing or stenosis of the neural foramen can be treated using a device configured to distract the facet joint.

In an aspect, an orthopedic implant, e.g., a distraction system, is described where the implant is anchored on opposite sides of a motion segment that would benefit from distraction. In an aspect, an expandable rod, screw, or other columnar adjustment mechanism is attached on opposite lateral sides of the motion segment. The length of the adjustment mechanism can be adjusted to determine the degree or amount of distraction. Additionally, a spring or shock-absorbing element can be included in the distraction device. In an aspect, such distraction device can provided with screws.

An aspect of the orthopedic implant is a rod anchored at each end across a motion segment that can be "switched" between dynamic distraction and rigid fixation in a minimally invasive, percutaneous, or non-invasive fashion. In an aspect, injection of a flowable material within the lumen of the device can cure and immobilize the components that allow for motion. Electrical current, heat, mechanical energy, or other techniques could also be used to render movable components fixed. Another method is insertion of a rigid implant axially along the length of the dynamic implant. This method of rendering a flexible orthopedic implant rigid can be applied to the design of other combination motion/fixation orthopedic implant, including disc, facet hip, knee, fingers shoulder, elbows, and ankle orthopedic implant.

The orthopedic implants as described herein include convertible or adjustable dynamic stabilization devices for joints. The stiffness or flexibility of the device can be altered or titrated after implantation to adapt the stiffness to a particular patient, and/or to adjust the stiffness over time, for example when laxity of the joint increases with age. The orthopedic implant, e.g., a dynamic stabilization implant, comprises a flexible coil contained in a tube member comprising telescoping tubes. The orthopedic implant can be used in a number of applications affixed across a joint motion segment to dynamically stabilize the joint. The coil can be energy absorbing. The coil can also be configured to exert a distracting force on the joint when implanted. The dynamic stabilization orthopedic implant can be converted to a rigid or more rigid orthopedic implant. The orthopedic implant includes a slit for receiving a rigid wire member. The rigid wire member is inserted into the slit to form the orthopedic implant from a dynamic orthopedic implant into a rigid orthopedic implant. As an alternative to a rigid wire member, a flexible coil of a selected stiffness can be inserted to change the stiffness of the dynamic orthopedic implant. The tube can alternatively comprise a ferromagnetic material contained therein and an electromagnetic field is applied that causes the orthopedic implant to become stiffer. The field can be varied to provide a variety of gradients in stiffness. The device can also include a sensor. Feedback can be provided and the stiffness of the orthopedic implant adjusted accordingly. The stiffness can be varied when implanted using patient feedback so that the implant is more or less flexible depending upon an individual patient's needs. In addition the stiffness can be changed at different times during the course of the implants lifetime. For example, the stiffness can be increased when an increased amount of stabilization is required.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an surgeon determines that speed and accuracy are paramount, the surgeon may opt for a mainly hardware and/or firmware vehicle; alternatively, if flexibility is paramount, the surgeon may opt for a mainly software implementation; or, yet again alternatively, the surgeon may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the surgeon, any of which may vary. Those skilled in the art will recognize that optical aspects of implementations will typically employ optically-oriented hardware, software, and or firmware.

In a general sense, the various aspects described herein can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art after reading the above description. The various aspects and embodiments disclosed herein are for purposes of illustration and are not intended to be limiting, with the true scope and spirit being indicated by the following claims.

What is claimed is:

1. An orthopedic implant comprising:
at least one adjustment mechanism configured for securing to at least one orthopedic structure of a subject, the at least one adjustment mechanism consisting of tension band wiring in combination with one or more of pins, screws, or intramedullary nails or rods;

at least six one motors directly connected to the at least one adjustment mechanism, wherein the at least six motors are configured to move the at least one adjustment mechanism in six degrees of freedom;

at least one ultrasonic actuator operably connected to the at least six motors, the ultrasonic actuator is operable to power the at least six motors from an energy source configured to be remote from the orthopedic implant and operably coupled to the at least one ultrasonic actuator via ultrasonic energy;

a controller and a transmitter;

a sensor in communication with the controller and the transmitter, the sensor including circuitry for detecting a change in at least one of strain, pressure, or position of the at least one adjustment mechanism of the orthopedic implant when operably secured to the at least one orthopedic structure;

the transmitter including circuitry for transcutaneously reporting to a network configured to be remote from the orthopedic implant, information from the sensor indicative of the detected change; the controller including circuitry for receiving energy from the remote energy source operably coupled to the at least one ultrasonic actuator via ultrasonic energy to remotely power the at least one motor to move the at least one adjustment mechanism of the orthopedic implant responsive to receiving reporting information indicative of the detected change in the at least one adjustment mechanism; and the controller including circuitry for transcutaneously receiving control commands from the remote network to the controller to cause movement of the at least one adjustment mechanism responsive to reporting information from the sensor and the transmitter indicative of the detected change to adjust the curvature of the at least one orthopedic structure.

2. The implant of claim 1, wherein the controller including the circuitry for transcutaneously receiving control commands to cause movement of the at least one adjustment mechanism includes the controller configured to receive an input signal from the transmitter to actuate the at least six motors.

3. The implant of claim 1, wherein the sensor including circuitry for detecting the change in at least one of strain, pressure, or position of the orthopedic structure includes the sensor configured to send an input signal to the transmitter.

4. The implant of claim 1, wherein the controller including the circuitry for transcutaneously receiving control commands includes the controller configured to control actuation of the at least six motors configured to maintain the at least one orthopedic structure in a defined position.

5. The implant of claim 1, wherein the controller including the circuitry for transcutaneously receiving control commands includes the controller configured to control actuation of the at least six motors to execute a sequence of two or more defined configurational changes to the at least one adjustment mechanism.

6. The implant of claim 1, wherein the controller including the circuitry for transcutaneously receiving control commands includes the controller configured to receive an input signal originating from human input.

7. The implant of claim 1, wherein the controller including the circuitry for transcutaneously receiving control commands includes the controller configured to receive an input signal originating from data input.

8. The implant of claim 7, wherein the data input is X-ray data, magnetic resonance imaging data, or ultrasound data.

9. The implant of claim 1, wherein the sensor including the circuitry for detecting the change in at least one of a strain, a pressure, or a position of an orthopedic structure includes the sensor configured to inform the controller in response to a sensed condition of the orthopedic structure.

10. The implant of claim 1, wherein the sensor including the circuitry for detecting the change in at least one of strain, pressure, or position of an orthopedic structure includes a strain gauge, accelerometer, piezoelectric film, Hall effect sensor, linear variable displacement transducer (LVDT), differential variable reluctance transducer (DVRT), or reed switch sensor.

11. The implant of claim 1, wherein the sensor including the circuitry for detecting the change in at least one of strain, pressure, or position of an orthopedic structure includes a sensor configured to detect health or integrity of the orthopedic structure.

12. The implant of claim 1, wherein the sensor including the circuitry for detecting the change in at least one of strain, pressure, or position of an orthopedic structure includes the sensor configured to detect ultrasound through the orthopedic structure or conductivity of the orthopedic structure.

13. The implant of claim 1, wherein the sensor including the circuitry for detecting the change in at least one of strain, pressure, or position of the orthopedic structure includes the sensor configured to detect an osteogenic cell marker.

14. The implant of claim 1, wherein the sensor including the circuitry for detecting the change in at least one of strain, pressure, or position of the orthopedic structure includes the sensor configured to detect an osteogenic cell marker on a mesenchymal stem cell or osteoblast.

15. The implant of claim 1, wherein the sensor including the circuitry for detecting the change in at least one of strain, pressure, or position of the orthopedic structure includes the sensor configured to detect alkaline phosphatase, osteocalcin, CBFA1/Osf2, or collagen 1A1.

16. The implant of claim 1, wherein the transmitter including the circuitry for transcutaneously reporting information indicative of the detected change to the remote network includes the transmitter in communication with the sensor and the controller, the transmitter configured to report activity of the implant to an external source.

17. The implant of claim 1, wherein the transmitter including the circuitry for transcutaneously reporting information indicative of the detected change to the remote network includes the transmitter configured to report activity of the implant to the remote network including a sensed condition of the orthopedic structure.

18. The implant of claim 1, wherein the transmitter including the circuitry for transcutaneously reporting information indicative of the detected change to the remote network includes the transmitter in communication with the sensor and the controller, the transmitter configured to send an actuation signal to the at least six motors.

19. The implant of claim 1, wherein the at least six motors are configured to be remotely-actuated from outside a body of a subject.

20. The implant of claim 1, wherein at least one of the at least six motors includes at least one of an electronic motor, electrostrictive motor, piezoelectric motor, ultrasonically-activated motor, shape memory alloy actuator, paraffin actuator, electromagnetic solenoid, or electroactive polymer.

21. The implant of claim 1, wherein at least one of the at least six motors includes a stepper motor, drive motor, or servomotor.

22. The implant of claim 1, wherein at least one of the at least six motors includes a piezoelectric stepper motor.

23. The implant of claim 1, wherein at least one of the at least six motors includes an ultrasonic lead screw motor.

24. The implant of claim 1, wherein the at least six motors includes an ultrasonically-activated motor configured to controllably move the at least one adjustment mechanism in at least six degrees of freedom to adjust curvature of the at least one orthopedic structure, wherein the orthopedic structure is a femur.

25. The implant of claim 1, wherein the at least six motors are configured to controllably move the at least one adjustment mechanism in at least six degrees of freedom to lengthen the at least one orthopedic structure, shorten the at least one orthopedic structure, tighten the at least one orthopedic structure, apply compression to the at least one orthopedic structure, twist the at least one orthopedic structure, shear the at least one orthopedic structure, increase or decrease stress or load on the at least one orthopedic structure.

26. The implant of claim 1, wherein the at least one adjustment mechanism is configured to be incrementally adjusted.

27. The implant of claim 1, wherein the orthopedic structure is bone.

28. The implant of claim 1, wherein the at least one adjustment mechanism is configured to be attached at a bone fracture site, bone graft, or fused bone.

29. The implant of claim 1, wherein at least one of the at least six motors is powered from an internal energy source including battery, capacitor, or mechanical storage.

30. A system comprising:
an indwelling orthopedic implant including:
at least one adjustment mechanism configured for securing to at least one orthopedic structure of a subject, the at least one adjustment mechanism consisting of tension band wiring in combination with one or more of pins, screws, or intramedullary nails or rods;
at least six motors directly connected to the at least one adjustment mechanism, wherein the at least six motors are configured to move the at least one adjustment mechanism in six degrees of freedom;
an energy source configured to be remote from the orthopedic implant and operably coupled to at least one ultrasonic actuator via ultrasonic energy to remotely power the at least six motors directly connected to the at least one adjustment mechanism;
wherein the at least one ultrasonic actuator is operably connected to the at least six motors, and the at least one ultrasonic actuator is operable to power the at least six motors from the remote energy source operably coupled via ultrasonic energy;
a controller and a transmitter;
a sensor in communication with the controller and the transmitter, the sensor including circuitry for detecting a change in an applied force or a change in position of the at least one adjustment mechanism when operably secured to a bone fracture site of a limb of a subject;
the controller including circuitry for transcutaneously receiving energy from the remote energy source operably coupled to the at least one ultrasonic actuator via ultrasonic energy to remotely power the at least motors directly connected to the at least one adjustment mechanism of the indwelling orthopedic implant responsive to reporting information from the sensor to the transmitter indicative of the detected change in an applied force or a change in position of the at least one adjustment mechanism when operably secured to the bone fracture site of the limb of the subject; and
the controller including circuitry for actuating the at least one adjustment mechanism in at least six degrees of freedom to adjust curvature of the limb of the subject responsive to reporting information indicative of the detected change in the applied force or the change in position of the at least one adjustment mechanism when operably secured to the bone fracture site of the limb of the subject.

31. The system of claim 30, wherein the controller including the circuitry for actuating the at least one adjustment mechanism includes the controller configured to receive an input signal from the transmitter to actuate the at least six motors.

32. The system of claim 31, wherein the sensor including the circuitry for detecting the change in an applied force or the change in position includes the sensor configured to send the input signal to the transmitter and to inform the controller in response to a sensed condition of the at least one adjustment mechanism.

33. The implant of claim 1, wherein the sensor including the circuitry for detecting the change in at least one of strain, pressure, or position of an orthopedic structure includes the sensor configured to detect flexibility or stiffness of the orthopedic implant.

* * * * *

UNITED STATES PATENT AND TRADEMARK OFFICE
CERTIFICATE OF CORRECTION

| | | |
|---|---|---|
| PATENT NO. | : 9,095,436 B2 | Page 1 of 1 |
| APPLICATION NO. | : 12/386269 | |
| DATED | : August 4, 2015 | |
| INVENTOR(S) | : Edward S. Boyden et al. | |

It is certified that error appears in the above-identified patent and that said Letters Patent is hereby corrected as shown below:

In the Claims

Column 36, Lines 14-15, Claim 30:

"ultrasonic energy to remotely power the at least motors. . ." should be

-- ultrasonic energy to remotely power the at least six motors. . . --

Signed and Sealed this
Twelfth Day of January, 2016

Michelle K. Lee
*Director of the United States Patent and Trademark Office*